US012745961B2

(12) United States Patent
Khoo et al.

(10) Patent No.: US 12,745,961 B2
(45) Date of Patent: Sep. 29, 2026

(54) VASCULAR GRAFT SYSTEM AND A METHOD OF PROCESSING AN ARTERIAL PRESSURE PULSE TRACE

(71) Applicants: CITY UNIVERSITY OF HONG KONG, Kowloon (HK); HONG KONG CENTRE FOR CEREBRO-CARDIOVASCULAR HEALTH ENGINEERING LIMITED, New Territories (HK)

(72) Inventors: Bee Luan Khoo, Hong Kong (HK); Haojun Hua, Kowloon (HK)

(73) Assignees: HONG KONG CENTRE FOR CEREBRO-CARDIOVASCULAR HEALTH ENGINEERING LIMITED, New Territories (HK); CITY UNIVERSITY OF HONG KONG, Kowloon (HK)

( * ) Notice: Subject to any disclaimer, the term of this patent is extended or adjusted under 35 U.S.C. 154(b) by 681 days.

(21) Appl. No.: 18/300,368

(22) Filed: Apr. 13, 2023

(65) Prior Publication Data

US 2023/0320664 A1 Oct. 12, 2023

Related U.S. Application Data

(63) Continuation-in-part of application No. 17/457,593, filed on Dec. 3, 2021, now Pat. No. 12,310,747.

(51) Int. Cl.
*A61B 5/00* (2006.01)
*A61B 5/0205* (2006.01)
(Continued)

(52) U.S. Cl.
CPC ............ *A61B 5/686* (2013.01); *A61B 5/0205* (2013.01); *A61B 5/0215* (2013.01);
(Continued)

(58) Field of Classification Search
CPC ..... A61B 5/686; A61B 5/0205; A61B 5/0215; A61B 5/4851; A61B 5/1459; A61B 5/29;
(Continued)

(56) References Cited

U.S. PATENT DOCUMENTS 11,918,384 B2 * 3/2024 Ghosh .................. A61B 5/0295
2016/0143546 A1 * 5/2016 McCombie .............. A61B 5/33
600/494

(Continued)

FOREIGN PATENT DOCUMENTS

CN 115227211 A 10/2022

OTHER PUBLICATIONS

Almeida VG, Vieira J, Santos P, Pereira T, Pereira HC, Correia C, Pego M, Cardoso J. Machine Learning Techniques for Arterial Pressure Waveform Analysis. Journal of Personalized Medicine. 2013; 3(2):82-101. (Year: 2013).*

(Continued)

*Primary Examiner* — Jason M Sims
*Assistant Examiner* — Noah M Healy
(74) *Attorney, Agent, or Firm* — Conley Rose, P.C.; Michael W. Piper; Gayatry S. Nair

(57) ABSTRACT

A vascular graft system comprising a vascular graft and a processing unit. The vascular graft comprises at least one pressure sensing device. The processing unit is connected to the at least one pressure sensing device. The processing unit comprises a processor which is configured to (a) receive an arterial pressure pulse trace from the pressure sensor which comprises pressure pulses, (b) classify each pulse as regular or irregular and remove the irregular pulses; and (c) for at least one of the pulses calculate at lease one of PWV, SI, K and AI. There is also disclosed an associated method of processing an arterial pressure pulse trace to obtain at least one of PWV, SI, K and AI.

18 Claims, 12 Drawing Sheets

(51) Int. Cl.

| | |
|---|---|
| ***A61B 5/0215*** | (2006.01) |
| ***A61B 5/29*** | (2021.01) |
| ***A61B 5/352*** | (2021.01) |
| ***A61F 2/06*** | (2013.01) |
| ***G16H 50/20*** | (2018.01) |
| *A61B 5/1459* | (2006.01) |

(52) U.S. Cl.

CPC .............. *A61B 5/4851* (2013.01); *A61F 2/06* (2013.01); *G16H 50/20* (2018.01); *A61B 5/1459* (2013.01); *A61B 5/29* (2021.01); *A61B 5/352* (2021.01); *A61B 2562/0247* (2013.01)

(58) Field of Classification Search

CPC ............ A61B 5/352; A61B 2562/0247; A61B 5/02405; A61B 5/0285; A61B 2562/028; A61B 2562/12; A61B 5/6876; A61B 5/7264; A61B 5/026; A61B 5/02158; A61B 5/02007; A61B 5/0245; A61F 2/06; A61F 2/07; A61F 2/82; A61F 2/95

See application file for complete search history.

(56) References Cited

U.S. PATENT DOCUMENTS

| | | | | |
|---|---|---|---|---|
| 2016/0262700 | A1* | 9/2016 | Kuraguntla .......... | A61B 5/6876 |
| 2021/0328130 | A1* | 10/2021 | Wang ...................... | B29C 70/62 |

OTHER PUBLICATIONS

Natta, L., Mastronardi, V.M., Guido, F et al. Soft and flexible piezoelectric smart patch for vascular graft monitoring based on Aluminum Nitride thin film. Sci Rep 9, 8392 (2019). (Year: 2019).*

Trachet, et al., "Numerical Validation of a New Method to Assess Aortic Pulse Wave Velocity from a Single Recording of a Brachial Artery Waveform with an Occluding Cuff", Annals of Biomedical Engineering, vol. 38, No. 3, Mar. 2010, 13 pages, DOI: 10.1007/s10439-010-9945-1.

Simonetti, et al., "Pulse contour analysis: a valid assessment of central arterial stiffness in children?", Pediatr Nephrol (2008) 23:439-444, DOI 10.1007/s00467-007-0693-x.

Millasseau, et al., "Determination of age-related increases in large artery stiffness by digital pulse contour analysis", Clinical Science (2002) 103, 371-377.

Li, et al., "Sensitive and Wearable Optical Microfiber Sensor for Human Health Monitoring", Adv. Mater. Technol. 2018, 3, 1800296, 8 pages, DOI: 10.1002/admt.201800296.

Brennan, et al., "Do Existing Measures of Poincaré Plot Geometry Reflect Nonlinear Features of Heart Rate Variability?", IEEE Transactions on Biomedical Engineering, vol. 48, No. 11, Nov. 2001, 6 pages.

Zhichang, et al., "A Research on Characteristic Information of Pulse Wave", Journal Of Beijing Polytechnic University, vol. 22, No. I, Mar. 1996, 9 pages.

Kaisti, et al., "Clinical assessment of a non-invasive wearable MEMS pressure sensor array for monitoring of arterial pulse waveform, heart rate and detection of atrial fibrillation", npj Digital Medicine (2019) 2:39, 10 pages, https://doi.org/10.1038/s41746-019-0117-x.

He, et al., "Deep Residual Learning for Image Recognition", 2016 IEEE Conference on Computer Vision and Pattern Recognition, 2016, 9 pages, DOI 10.1109/CVPR.2016.90.

Simonyan, et al., "Very Deep Convolutional Networks for Large-Scale Image Recognition", Published as a conference paper at ICLR 2015, Apr. 10, 2015, 14 pages.

Fang, et al., "Ambulatory Cardiovascular Monitoring Via a Machine-Learning-Assisted Textile Triboelectric Sensor", Adv. Mater. 2021, 33, 2104178, 8 pages, DOI: 10.1002/adma.202104178.

Ghatak, et al., "Poincare parameters and principal component analysis of Heart rate variability of subjects with health disorder", Feb. 28, 2018, 27 pages, physics.med-ph, arXiv:1802.10289v1.

Malik, "Heart Rate Variability Standards of Measurement, Physiological Interpretation, and Clinical Use—Task Force of the European Society of Cardiology the North American Society of Pacing Electrophysiology", Circulation, vol. 93, Issue 5, Mar. 1, 1996, pp. 1043-1065, https://doi.org/10.1161/01.CIR.93.5.1043.

Bergfeldt, et al., "Power spectral and Poincare plot characteristics in sinus node dysfunction", J Appl Physiol, vol. 94, 2217-2224, Jun. 2003.

* cited by examiner

VASCULAR GRAFT SYSTEM AND A METHOD OF PROCESSING AN ARTERIAL PRESSURE PULSE TRACE

CROSS-REFERENCE TO RELATED APPLICATIONS

This application is a continuation-in-part application of U.S. application Ser. No. 17/457,593 filed on 3 Dec. 2021, the disclosure of which is hereby incorporated by reference in its entirety.

TECHNICAL FIELD OF THE INVENTION

The present invention relates to a vascular graft system. The present invention also relates to a method of processing an arterial pressure pulse trace.

BACKGROUND

Vascular grafts are known. During a surgical procedure, a vascular graft comprising a shape of a hollow cylinder can be connected to two blood vessels such that after the vascular graft is connected to the two blood vessels, the blood flow from one of the two blood vessels is directed through the vascular graft and from the vascular graft to the other one of the two blood vessels. It is generally desirable to obtain reliable information about the condition of the flow paths along which blood flows in an easy manner, particularly after a vascular graft has been implanted.

An object of the invention is to provide a solution to obtain reliable information about the condition of the flow paths along which blood flows in an easy manner, particularly after a vascular graft has been implanted.

SUMMARY OF THE INVENTION

Accordingly, in a first aspect, the present invention provides a vascular graft system comprising a vascular graft, the vascular graft comprising

- a flexible substrate, which can assume an unrolled configuration, in which the substrate extends along a main extension plane, and a rolled-up configuration in which a first surface of the substrate on a first side of the substrate is facing radially inward and a second surface of the substrate on a second side of the substrate is facing radially outward; and,
- at least one pressure sensing device, which is arranged on the first side of the substrate and comprises a first electrode, a second electrode, and a piezoelectric element arranged between the first electrode and the second electrode, and, a processing unit connected to the at least one pressure sensing device, the processing unit comprising a processor configured to perform the steps of (a) receive an arterial pressure pulse trace from the pressure sensor, the arterial pressure pulse trace comprising a set of consecutive pressure pulses;

(b) for each pulse in the set of pressure pulses classify the pulse as a regular pulse or an irregular pulse and remove the pulse from the set of pressure pulses if the pulse is an irregular pulse so producing a reduced set of pressure pulses;

(c) for at least one of the pressure pulses in the reduced set of pressure pulses determine at least one of PWV, SI, K and AI;

and, (d) compare the determined at least one of PWV, SI, K and AI to at least one known value.

The vascular graft system according to the invention enables accurate measurement of at least one of PWV, SI and AI to be made and compared with known results.

The vascular graft comprises a flexible substrate. The flexibility of the substrate ensures that the substrate can assume an unrolled configuration and a rolled-up configuration and can transfer from the unrolled configuration to the rolled-up configuration and from the rolled-up configuration to the unrolled configuration.

The flexible substrate can assume the unrolled configuration, in which the substrate extends along the main extension plane, and the rolled-up configuration, in which the first surface of the substrate on the first side of the substrate is facing radially inward and the second surface of the substrate on the second side of the substrate is facing radially outward. Particularly, during a surgical procedure, the vascular graft can be provided in the unrolled configuration and can be brought into the rolled-up configuration to be connected to two blood vessels such that after the vascular graft is connected to the two blood vessels, the blood flow from one of the two blood vessels is directed through the vascular graft and from the vascular graft to the other one of the two blood vessels. The unrolled configuration ensures that the vascular graft can be transported in a space saving way, particularly if the vascular graft is transported together with other vascular grafts, which are also in the unrolled configuration. Preferably, the flexible substrate assuming the unrolled configuration is the same as the vascular graft assuming the unrolled configuration. Similarly, it is preferred that the flexible substrate assuming the rolled-up configuration is the same as the vascular graft assuming the rolled-up configuration. Since in the rolled-up configuration, the first surface of the substrate is facing radially inward, the blood flows along the first surface. For example, the blood flows along an axial direction of the substrate in the rolled-up configuration.

The vascular graft further comprises the at least one pressure sensing device. Each pressure sensing device is preferably adapted to provide signals which comprise information from which the pressure of the blood, particularly the static pressure of the blood, can be inferred. The vascular graft may comprise one pressure sensing device or multiple pressure sensing devices. The features, technical effects and/or advantages described in connection with one pressure sensing device also apply to each of the pressure sensing devices at least in an analogous manner, so that no corresponding repetition is made here.

The at least one pressure sensing device is arranged on the first side of the substrate and comprises the first electrode, the second electrode, and the piezoelectric element arranged between the first electrode and the second electrode. Since the at least one pressure sensing device is arranged on the first side of the substrate, the at least one pressure sensing device is facing radially inward on the side of the substrate facing the blood flow through the vascular graft. Depending on the pressure of the blood, particularly the static pressure of the blood, the blood arranged inside the vascular graft applies a particular mechanical load onto each of the pressure sensing devices. The applied mechanical load onto a particular pressure sensing device implies that a mechanical stress is applied to the piezoelectric element of the pressure sensing device and the mechanical stress applied to the piezoelectric element results in a variation of the electric field extending between the surfaces of the piezoelectric element. From the electric field extending between the surfaces of the piezoelectric element the pressure of the blood can be inferred. Preferably, each surface of the piezoelectric element extends in parallel to the main extension plane. Preferably, one of the surfaces of the piezoelectric element is attached to a surface of the first electrode of the pressure sensing device. Preferably, the other one of the surfaces of the piezoelectric element is attached to a surface of the second electrode of the pressure sensing device. The pressure of the blood may vary over time due to the heart muscle pumping blood through the vascular graft. For each point in time, depending on the current pressure of the blood, particularly the static pressure of the blood, the blood applies a particular mechanical load onto each of the pressure sensing devices.

The vascular graft may further comprise at least one velocity sensing device which is arranged on the first side of the substrate and comprises a first electrode, a second electrode and a piezoelectric element arranged between the first electrode and the second electrode. Each velocity sensing device is preferably adapted to provide signals which comprise information from which the velocity of the blood can be inferred. The vascular graft may comprise one velocity sensing device or multiple velocity sensing devices. The features, technical effects and/or advantages described in connection with one velocity sensing device also apply to each of the velocity sensing devices at least in an analogous manner, so that no corresponding repetition is made here.

Since the at least one velocity sensing device is arranged on the first side of the substrate, the at least one velocity sensing device is facing radially inward on the side of the substrate facing the blood flow through the vascular graft. Depending on the velocity of the blood, the blood applies a particular mechanical load onto each of the velocity sensing devices. The applied mechanical load onto a particular velocity sensing device implies that a mechanical stress is applied to the piezoelectric element of the velocity sensing devices and the mechanical stress applied to the piezoelectric element results in a variation of the electric field extending between the surfaces of the piezoelectric element. From the electric field extending between the surfaces of the piezoelectric element the velocity of the blood can be inferred. Preferably, each surface of the piezoelectric element extends in parallel to the main extension plane. Preferably, one of the surfaces of the piezoelectric element is attached to a surface of the first electrode of the velocity sensing device. Preferably, the other one of the surfaces of the piezoelectric element is attached to a surface of the second electrode of the velocity sensing device. The velocity of the blood may vary over time due to the heart muscle pumping blood through the vascular graft. For each point in time, depending on the current velocity of the blood, particularly depending on the current difference between the velocity of the blood at a radially inner side and the velocity of the blood at a radially outer side, the blood applies a particular mechanical load onto each of the velocity sensing devices.

Therefore, the vascular graft is adapted to provide information from which the pressure and the velocity of the blood can be determined, particularly at certain positions in the vascular graft at which the pressure and velocity sensing devices are arranged. For example, information about the cross section available for the blood to flow through the vascular graft can be derived from the pressure and the velocity of the blood at certain positions in the vascular graft. For example, the location, size, and morphology (e.g., shape of a triangle, semi-circle, or rectangle) of a thrombus arranged radially inward of the first surface can be derived.

In summary, the vascular graft system allows one to obtain reliable information about the condition of the flow paths along which blood flows in an easy manner, particularly after the vascular graft of the vascular graft system has been implanted.

Preferably the processor is configured to determine at least one of AWV, SI, K and AI for a plurality of pressure pulses.

Preferably the processor is configured such that for at least one pressure pulse it determines each of PWV, SI, K and AI.

Preferably the processor comprises an artificial neural network configured to classify the pressure pulses as irregular or regular.

Preferably the processor is configured to classify the pressure pulses by comparing each pressure pulse with at least one pre-classified pressure pulse.

Preferably the processor is further configured to perform the steps of (a) for each pressure pulse, i, determine the time interval $RR_i$ between the $i^{th}$ pressure pulse and the $(i+1)^{th}$ pressure pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) compare SD1 to SD2 to obtain a pressure result.

Preferably the vascular graft system further comprises at least one electrode connected to the processing unit for providing an ECG trace to the processor, the ECG trace comprising a set of consecutive ECG pulses, the processor being further configured to perform the steps of (a) for each ECG pulse, i, determine the time interval $RR_i$ between the $i^{th}$ ECG pulse and the ECG pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) compare SD1 to SD2 to obtain an ECG result.

Preferably the vascular graft system further comprises at least one pulse oximeter connected to the processing unit for providing a PPG trace to the processor, the PPG trace comprising a set of consecutive PPG pulses, the processor being further configured to perform the steps of (a) for each PPG pulse, i, determine the time interval $RR_i$ between the $i^{th}$ PPG pulse and the $(i+1)^{th}$ PPG pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) compare SD1 to SD2 to obtain a PPG result.

In a further aspect of the invention there is provided a method of processing an arterial pressure pulse trace comprising the steps of (a) receiving an arterial pressure pulse trace from a vascular graft, the vascular graft comprising at least one pressure sensing device, the arterial pressure pulse trace comprising a set of consecutive pressure pulses;

(b) for each pressure pulse in the set of pressure pulses classifying the pulse as a regular pulse or an irregular pulse and removing the pulse from the set of pressure pulses if the pulse is an irregular pulse so producing a reduced set of pressure pulses;

(c) for at least one of the pressure pulses in the reduced set of pressure pulses determining at least one of PWV, SI, K and AI;

and, (d) comparing the determined at least one of PWV, SI, K and AI to at least one known value.

Preferably the vascular graft comprises a flexible substrate, which can assume an unrolled configuration, in which the substrate extends along a main extension plane, and a rolled-up configuration in which a first surface of the substrate on a first side of the substrate is facing radially inward and a second surface of the substrate on a second side of the substrate is facing radially outward;

the at least one pressure sensing device being arranged on the first side of the substrate and comprising a first electrode, a second electrode, and a piezoelectric element arranged between the first electrode and the second electrode.

Preferably the vascular graft further comprises at least one velocity sensing device which is arranged on the first side of the substrate and comprises a first electrode, a second electrode, and a piezoelectric element arranged between the first electrode and the second electrode.

Preferably the step of for at least one of the pressure pulses in the reduced set of pressure pulses determining at least one of PWV, SI, K and AI comprises determining at least one of AWV, SI, K and AI for a plurality of pressure pulses.

Preferably the step of for at least one of the pressure pulses in the reduced set of pressure pulses determining at least one of PWV, SI, K and AI comprises determining each of AWV, SI, K and AI for at least one pressure pulse.

Preferably the step of for each pressure pulse in the set of pressure pulses classifying the pulse as a regular pulse or an irregular pulse comprises providing each pulse to an artificial neural network for classification.

Preferably the step of for each pressure pulse in the set of pressure pulses classifying the pulse as a regular pulse or an irregular pulse comprises comparing each pulse with at least one pre-classified pressure pulse.

Preferably the method further comprises the steps of (a) for each pressure pulse, i, determining the time interval $RR_i$ between the $i^{th}$ pressure pulse and the $(i+1)^{th}$ pressure pulse;

(b) for the two sets of time intervals $$X=\{RR_i/i=1,2,3, \ldots n\}$$

$$Y=\{RR_{i+1}/1=1,2,3, \ldots n\}$$

determining SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) comparing SD1 to SD2 to obtain a pressure result.

Preferably the method further comprises the steps of (a) receiving a ECG trace, the ECG trace comprising a set of consecutive ECG pulses;

(b) for each ECG pulse, i, determining the time interval $RR_i$ between the $i^{th}$ ECG pulse and the $(i+1)^{th}$ ECG pulse;

(c) for the two sets of time intervals $$X=\{RR_i/i=1,2,3, \ldots n\}$$

$$Y=\{RR_{i+1}/i=1,2,3, \ldots n\}$$

determining SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (d) comparing SD1 to SD2 to obtain an ECG result.

Preferably the method further comprises the steps of (a) receiving a PPG trace, the PPG trace comprising a set of consecutive PPG pulses;

(b) for each PPG pulse, i, determining the time interval $RR_i$ between the $i^{th}$ PPG pulse and the $(i+1)^{th}$ PPG pulse;

(c) for the two sets of time intervals $$X=\{RR_i/i=1,2,3, \ldots n\}$$

$$Y=\{RR_{i+1}/i=1,2,3, \ldots n\}$$

determining SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (d) comparing SD1 to SD2 to obtain a PPG result.

According to a preferred embodiment of a vascular graft of the vascular graft system, the substrate comprises in the unrolled configuration a rectangular shape and in the rolled-up configuration a cylindrical shape, preferably the shape of a hollow cylinder. The rectangular shape allows the vascular graft to be manufactured together with other vascular grafts on a single wafer in a resource-efficient and material-saving manner. The cylindrical shape may depart from a perfect cylindrical shape in such a way that the shape of substrate comprises sections arranged one next to the other along the direction of blood flow, wherein each section comprises a cylindrical shape. Particularly, the cylindrical shape also includes any shapes the substrate may assume while being connected to two blood vessels.

According to a preferred embodiment of a vascular graft of the vascular graft system, the substrate comprises Polydimethylsiloxane, PDMS. The substrate may be made of PDMS. PDMS provides a material that ensures a flexibility of the substrate which is similar to the flexibility of blood vessels such that the mechanical properties of a vascular graft with a substrate comprising PDMS is particularly compatible with the mechanical properties of blood vessels.

According to a preferred embodiment of a vascular graft of the vascular graft system, each pressure sensing device is formed of a layer stack comprising multiple layers, wherein, when the substrate is in the unrolled configuration, each layer extends in parallel to the main extension plane, wherein a first layer of the multiple layers comprises the first electrode, a second layer of the multiple layers comprises the piezoelectric element, and a third layer of the multiple layers comprises the second electrode. In case each pressure sensing device is formed of a layer stack comprising multiple layers, each layer of the pressure sensing device can be manufactured with techniques known to manufacture layers for microelectromechanical systems. In case each layer extends in parallel to the main extension plane, the layers can be manufactured one after the other with techniques known to manufacture layers for microelectromechanical systems, which provides a vascular graft that can be manufactured in a time efficient manner. Further, in case the vascular graft comprises multiple pressure sensing devices, the layers of the pressures sensing devices can be manufactured in parallel, which provides a vascular graft that can be manufactured in a time efficient manner.

According to a preferred embodiment of a vascular graft of the vascular graft system, a fourth layer of the layer stack comprises a flexible layer arranged between the substrate and the first electrode. The flexibility of the flexible layer ensures that the flexible layer can assumed a deformed configuration, particularly if the substrate assumes the rolled-up configuration, and can reduce the deformation of the first electrode in the rolled-up configuration reducing the mechanical load on the first electrode, which increases the service life of the vascular graft.

According to a preferred embodiment of a vascular graft of the vascular graft system, each pressure sensing device comprises in the unrolled configuration a rectangular shape, the rectangular shape comprises preferably an extension along a first direction parallel to the main extension plane of 0.2 to 1.5 mm, preferably 1 mm, and an extension along a second direction parallel to the main extension plane and perpendicular to the first direction of 0.2 to 1 mm, preferably 0.5 mm. The rectangular shape allows each pressure sensing device to be manufactured with the assistance of techniques to manufacture microelectromechanical systems (MEMS), including known structuring steps.

According to a preferred embodiment of a vascular graft of the vascular graft system, each pressure sensing device is adapted to detect pressures from 0 to 40 kPa. Preferably, each pressure sensing device is adapted detect blood pressures of 0 kPa, 40 kPa, and each value between 0 kPa and 40 kPa.

According to a preferred embodiment of a vascular graft of the vascular graft system, each velocity sensing device comprises a cantilever, which comprises the piezoelectric element of the respective velocity sensing device. Depending on the velocity of the blood, the blood applies a particular mechanical load onto the cantilever. The applied mechanical load onto the cantilever implies that a mechanical stress is applied to the piezoelectric element of the velocity sensing device and the mechanical stress applied to the piezoelectric element results in a variation of the electric field extending between the surfaces of the piezoelectric element. Preferably, each cantilever is surrounded by blood from a radially inner side and a radially outer side. It is preferred that due to the blood flow through the vascular graft, the velocity of the blood at the radially inner side of the cantilever may be higher than the velocity of the blood at the radially outer side of the cantilever, or, alternatively, the velocity of the blood at the radially inner side of the cantilever may be lower than the velocity of the blood at the radially outer side of the cantilever. Therefore, the static pressure of the blood at the radially outer side of the cantilever may be higher than the static pressure of the blood at the radially inner side of the cantilever. Alternatively, the static pressure of the blood at the radially outer side of the cantilever may be lower than the static pressure of the blood at the radially inner side of the cantilever. Therefore, the cantilever may bend towards the radially inner side of the cantilever in case the velocity of the blood at the radially inner side of the cantilever is higher than the velocity of the blood at the radially outer side of the cantilever. Alternatively, the cantilever may bend towards the radially outer side of the cantilever in case the velocity of the blood at the radially inner side of the cantilever is lower than the velocity of the blood at the radially outer side of the cantilever. The velocity of the blood may vary over time due to the heart muscle pumping blood through the vascular graft. For each point in time, depending on the current velocity of the blood, particularly depending on the current difference between the velocity of the blood at the radially inner side of the cantilever and the velocity of the blood at the radially outer side of the cantilever, the blood applies a particular mechanical load onto each of the velocity sensing devices, particularly on each of the cantilevers.

According to a preferred embodiment of a vascular graft of the vascular graft system, in the unrolled configuration, the cantilever extends from a supported end in parallel to the main extension plane towards a free end such that, in the rolled-up configuration, the free end is positioned radially inward of a portion of a wall defining a recess formed in the flexible substrate, wherein the recess is open towards the first side of the substrate. Preferably, each pair of cantilever and recess is adapted such that blood can enter the recess. Therefore, each cantilever may be surrounded by blood from a radially inner side of the cantilever and a radially outer side of the cantilever. Due to the blood flow through the vascular graft and the recess, the velocity of the blood at the radially inner side of the cantilever may be higher than the velocity of the blood at the radially outer side of the cantilever, e.g., the velocity of the blood in the recess.

Therefore, the static pressure of the blood at the radially outer side of the cantilever may be higher than the static pressure of the blood at the radially inner side of the cantilever. Therefore, the cantilever may bend towards the radially inner side of the cantilever in case the velocity of the blood at the radially inner side of the cantilever is higher than the velocity of the blood at the radially outer side of the cantilever. The velocity of the blood may vary over time due to the heart muscle pumping blood through the vascular graft. For each point in time, depending on the current velocity of the blood, particularly depending on the current difference between the velocity of the blood at the radially inner side of the cantilever and the velocity of the blood at the radially outer side of the cantilever, the blood applies a particular mechanical load onto each of the velocity sensing devices, particularly on each of the cantilevers.

According to a preferred embodiment of a vascular graft of the vascular graft system, each velocity sensing device is formed of a layer stack comprising multiple layers, wherein, when the substrate is in the unrolled configuration, each layer extends in parallel to the main extension plane, wherein a first layer of the multiple layers comprises the first electrode, a second layer of the multiple layers comprises the piezoelectric element, and a third layer of the multiple layers comprises the second electrode. In case each velocity sensing device is formed of a layer stack comprising multiple layers, each layer of the velocity sensing device can be manufactured with techniques known to manufacture layers for microelectromechanical systems. In case each layer extends in parallel to the main extension plane, the layers can be manufactured one after the other with techniques known to manufacture layers for microelectromechanical systems, which provides a vascular graft that can be manufactured in a time efficient manner. Further, in case the vascular graft comprises multiple velocity sensing devices, the layers of the velocity sensing devices can be manufactured in parallel, which provides a vascular graft that can be manufactured in a time efficient manner. Further, in case the vascular graft comprises multiple pressure sensing devices and multiple velocity sensing devices, the layers of the pressure sensing devices and the layers of the velocity sensing devices can be manufactured in parallel, which provides a vascular graft that can be manufactured in a very time efficient manner.

According to a preferred embodiment of a vascular graft of the vascular graft system, a fourth layer of the layer stack comprises a flexible layer arranged between the substrate and the first electrode. The flexibility of the flexible layer ensures that the flexible layer can assumed a deformed configuration, particularly if the substrate assumes the rolled-up configuration, and can reduce the deformation of the first electrode in the rolled-up configuration reducing the mechanical load on the first electrode, which increases the service life of the vascular graft.

According to a preferred embodiment of a vascular graft of the vascular graft system, the recess comprises in the unrolled configuration a shape of a rectangular cuboid, the rectangular cuboid comprises preferably an extension along a first direction parallel to the main extension plane of 0.5 to 1.5 mm, preferably 1 mm, an extension along a second direction parallel to the main extension plane and perpendicular to the first direction of 0.5 to 1 mm, preferably 0.8 mm, and an extension along a third direction perpendicular to the main extension plane of 0.2 to 1 mm, preferably 0.5 mm. The shape of a rectangular cuboid allows each velocity sensing device to be manufactured with the assistance of techniques to manufacture microelectromechanical systems (MEMS), including known structuring steps.

According to a preferred embodiment of a vascular graft of the vascular graft system, each velocity sensing device comprises in the unrolled configuration a square shape, the square shape comprises preferably an extension along a first direction parallel to the main extension plane of 0.2 to 1.5 mm, preferably 0.5 mm, and an extension along a second direction parallel to the main extension plane and perpendicular to the first direction of 0.2 to 1.5 mm, preferably 0.5 mm. The square shape allows each velocity sensing device to be manufactured with the assistance of techniques to manufacture microelectromechanical systems (MEMS), including known structuring steps.

According to a preferred embodiment of a vascular graft of the vascular graft system, each velocity sensing device is adapted to detect flow velocities from 0 to 1000 ml/min. Preferably, each velocity sensing device is adapted detect blood flow velocities of 0 ml/min, 1000 ml/min, and each value between 0 ml/min and 1000 ml/min.

According to a preferred embodiment of a vascular graft of the vascular graft system, the piezoelectric element of the pressure sensing device comprises polyvinylidene difluoride, PVDF, and/or the piezoelectric element of the velocity sensing device comprises polyvinylidene difluoride, PVDF. Each piezoelectric element may be made of PVDF. PVDF provides a material that allows to use piezoelectricity to detect pressures and velocities of blood with a vascular graft.

According to a preferred embodiment of a vascular graft of the vascular graft system, the thickness of the piezoelectric element of the pressure sensing device and/or the thickness of the piezoelectric element of the velocity sensing device perpendicular to the main extension plane is 2 to 20 μm, preferably 4 μm. The thickness of the piezoelectric element of the pressure sensing device and/or the thickness of the piezoelectric element of the velocity sensing device perpendicular to the main extension plane is 2 to 20 μm, preferably 4 μm, resulted in particularly precise measurements of the pressures and velocities of the blood.

According to a preferred embodiment of a vascular graft of the vascular graft system, the flexible layer of the pressure sensing device comprises polyamide, PI, and/or the flexible layer of the velocity sensing device comprises polyamide, PI. Each flexible layer may be made of PI. PI provides a material that resulted in a particularly strong bond to the substrate and to the first electrode and resulted in a particular increase in service life of the vascular graft.

According to a preferred embodiment of a vascular graft of a vascular graft system, wherein the thickness of the flexible layer of the pressure sensing device and/or the thickness of the flexible layer of the velocity sensing device perpendicular to the main extension plane is 2 to 25 μm, preferably 8 μm. A thickness of the flexible layer of the pressure sensing device and/or a thickness of the flexible layer of the velocity sensing device perpendicular to the main extension plane is 2 to 25 μm, preferably 8 μm, resulted in a particularly long service life of the vascular graft.

According to a preferred embodiment of a vascular graft of the vascular graft system, wherein each pressure sensing device and each velocity sensing device are arranged on the first side of the substrate such that, in the rolled-up configuration, the pressure sensing and velocity sensing devices are arranged along a line, preferably with a distance between the devices along the line of 1 to 10 mm, particularly preferred 5 mm, wherein the line extends along an axial direction of the substrate and is parallel to the axis around which the substrate is rolled up in the rolled-up configuration. In case the pressure sensing and velocity sensing devices are arranged along the line, which extends along the axial direction of the substrate allows to detect pressures and velocities at different positions along the axial direction of the substrate.

According to a preferred embodiment of a vascular graft of the vascular graft system, the vascular graft further comprises electrically conductive paths, wherein each of the paths is coupled with one end, e.g., a first end, to one of the elements comprising the first electrode of the pressure sensing device, the second electrode of the pressure sensing device, the first electrode of the velocity sensing device, and the second electrode of the velocity sensing device, wherein each of the paths extends in a meandering shape from the respective first end to a respective second end. The meandering shape of each of the electrically conductive paths allows to employ electrically conductive materials as materials to form the electrically conductive paths, such as metals, and still allow the vascular graft to be flexible enough to assume the rolled-up configuration from the unrolled configuration.

According to a preferred embodiment of a vascular graft of the vascular graft system, the vascular graft further comprises a flexible encapsulation layer, which is arranged on the first side of the substrate such that, in the rolled-up configuration, the flexible encapsulation layer is arranged radially inward of each of the pressure sensing devices, each of the velocity sensing devices, and/or each of the electrically conductive paths. The encapsulation layer may provide a protection of each of the pressure sensing devices, each of the velocity sensing devices, and/or each of the electrically conductive paths against blood and/or water. Further, the encapsulation layer may provide an electrical insulation of each of the pressure sensing devices, each of the velocity sensing devices, and/or each of the electrically conductive paths against blood and/or water.

According to a preferred embodiment of a vascular graft of the vascular graft system, the encapsulation layer comprises parylene, preferably a chlorinated parylene, particularly preferred parylene C. The encapsulation layer may be made of parylene, preferably a chlorinated parylene, particularly preferred parylene C. Parylene, preferably a chlorinated parylene, particularly preferred parylene C, provides a material that resulted in a particularly strong bond to each of the pressure sensing devices, particularly to each of the second electrode of the pressure sensing devices, to each of the velocity sensing devices, particularly to each of the second electrode of the velocity sensing devices, and/or to each of the electrically conductive paths.

According to a preferred embodiment of a vascular graft of the vascular graft system, wherein the thickness of the encapsulation layer perpendicular to the main extension plane is 1 to 10 μm, preferably μm. A thickness of the encapsulation layer perpendicular to the main extension plane of 1 to 10 μm, preferably 5 μm, resulted in a particularly long service life of the vascular graft.

The vascular graft can be manufactured according to a method of manufacturing the vascular graft described as follows. The method may comprise eight steps (steps (a) to (h)). Particularly, the vascular graft may be manufactured with the assistance of techniques to manufacture microelectromechanical systems (MEMS). In step (a), a single-polished silicon wafer may be cleaned with acetone and/or ethyl alcohol. In step (b), Polyimide (PI) may be spin-coated on the silicon wafer and may be heated in a hot oven at 280° C. for 10 min to form a PI film. In step (c), a sputter-coating Au/Cr (160/40 nm) layer may be deposited onto the PI film through a shadow mask. In step (d), a piezoelectric PVDF layer may be fabricated. The fabrication of the PVDF layer may comprise dissolving PVDF powder in dimethylformamide with a weight fraction of, e.g., 15 wt. % (weight percent). The fabrication of the PVDF layer may further comprise exposing the surface of the PI layer fabricated in step (b) and the surface of the Au/Cr layer on the PI layer fabricated in step (c) to oxygen plasma for 60 s before spin-coating of PVDF to increase the interfacial adhesion both between the PI layer and the PVDF layer and between the Au/Cr layer and the PVDF layer. After spin-coating, the PVDF film may be heated using a hot plate at 30° C. for 30 min and may then be annealed at 100° C. for 2 h with a vacuum drying oven to improve the 8-phase crystallinity. In step (e), a sputter-coating Au/Cr (160/40 nm) layer may be deposited onto the PVDF layer through a shadow mask. In step (f), the layers deposited on top of the silicon wafer may be patterned by a reactive ion etching, RIE, process during which a layer of positive photoresist may be employed as a mask. In step (g), water-soluble tapes, WSTs, may be used as stamps to pick up the patterned layers. In step (h), a flexible Polydimethylsiloxane, PDMS, substrate may be fabricated by a PDMS molding process. Negative molds of the required size of the substrate may be fabricated by a rapid prototyping process. The PDMS substrate may be peeled out of the molds after PDMS casting. The PDMS substrate may then bonded to the patterned layers. PDMS substrate and the WST may be exposed to UV-induced ozone, which creates chemical groups between the patterned layers and the PDMS substrate to enhance bonding strength. The patterned layers may be attached to the PDMS substrate and the WST, the patterned layers, and the PDMS substrate may be heated in an oven at 70° C. for 10 min, which formed strong bonding between the PDMS substrate and the patterned layers. The WST, the patterned layers, and the PDMS substrate may be immersed in water to remove WSTs. An encapsulation layer may be formed on top of the patterned layers and the PDMS. A uniform encapsulation layer may be formed by employing a vacuum evaporator and a 5 μm thick parylene C encapsulation layer may be formed to provide a protection against blood and water and an electrical insulation. A dilute isopropyl alcohol-water solution of organic silane gamma-methacrylxypropyltrimethoxysilane may be used before parylene C deposition to improve the adhesion significantly. After the deposition of the encapsulation layer, the vascular graft may be put on a hot plate at 100° C., and a voltage of 60 V/μm may be applied to the lead pads to polarize the piezoelectric PVDF elements 19. After polarization treatment, the lead pads may be short-circuited for 24 h.

BRIEF DESCRIPTION OF THE DRAWINGS

Further features, advantages and application possibilities of the present invention may be derived from the following description of exemplary embodiments and/or the figures. Thereby, all described and/or visually depicted features for themselves and/or in any combination may form an advantageous subject matter and/or features of the present invention independent of their combination in the individual claims or their dependencies. Furthermore, in the figures, same reference signs may indicate same or similar objects.

DESCRIPTION OF EMBODIMENTS

Figure 1A:
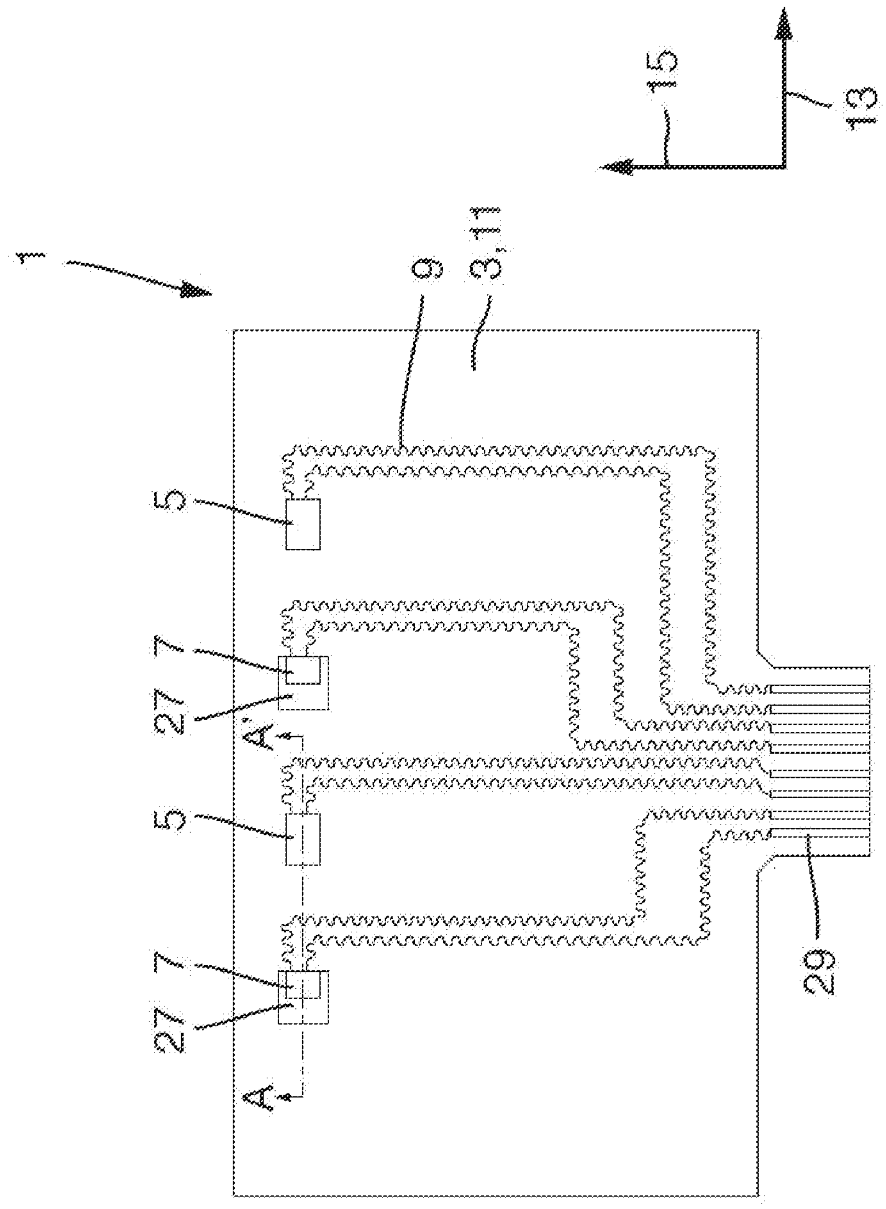
FIGS. 1(*a*) and 1(*b*) schematically illustrates an embodiment of a vascular graft of a vascular graft system according to the invention in an unrolled configuration.
Figure 1B:
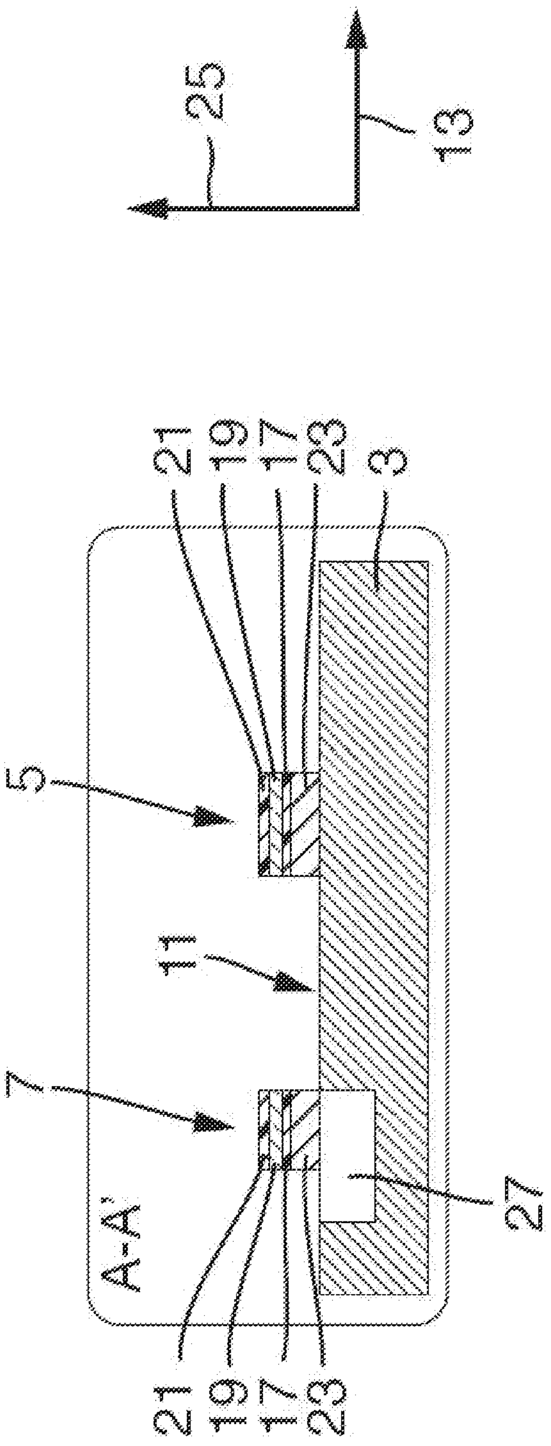

FIGS. 1(*a*) and 1(*b*) schematically illustrate an embodiment of a vascular graft 1 of a vascular graft system according to the present invention. The vascular graft 1 comprises a flexible substrate 3, two pressure sensing devices 5, two velocity sensing devices 7, and electrically conductive paths 9.

The flexible substrate 3 can assume an unrolled configuration, in which the substrate extends along a main extension plane. The unrolled configuration is shown in FIGS. 1(*a*) and 1(*b*). FIG. 1 (*a*) is a view onto a first surface 11 of the substrate 3 on a first side of the substrate 3. The two pressure sensing devices and the two velocity sensing devices 7 are arranged on the first side of the substrate 3. The substrate 3 comprises in the unrolled configuration shown in FIG. 1(*a*) a rectangular shape, which is visible in the view perpendicular to the main extension plane and onto the first surface 11 in FIG. 1 (*a*). The substrate 3 comprises Polydimethylsiloxane, PDMS.

Each pressure sensing device 5 comprises in the unrolled configuration shown in FIGS. 1(*a*) and 1(*b*) a rectangular shape. The rectangular shape comprises an extension along a first direction 13 parallel to the main extension plane of 0.2 to 1.5 mm, preferably 1 mm, and an extension along a second direction 15 parallel to the main extension plane and perpendicular to the first direction 13 of 0.2 to 1 mm, preferably 0.5 mm. Each pressure sensing device 5 is adapted to detect pressures from 0 to 40 kPa. Each velocity sensing device 7 comprises in the unrolled configuration shown in FIGS. 1(*a*) and 1(*b*) a square shape. The square shape comprises an extension along the first direction 13 of 0.2 to 1.5 mm, preferably 0.5 mm, and an extension along the second direction 15 of 0.2 to 1.5 mm, preferably 0.5 mm. Each velocity sensing device 7 is adapted to detect flow velocities from 0 to 1000 ml/min.

FIG. 1 (*b*) is a sectional view along the line A-A' in FIG. 1 (*a*). FIG. 1 (*b*) shows one pressure sensing device 5 and one velocity sensing device 7. The paths 9 are not displayed in FIG. 1 (*b*). The pressure sensing device 5 and the velocity sensing device 7 shown in FIG. 1(*b*) are shown as examples and each pressure sensing device 5 of the vascular graft 1 and each velocity sensing device 7 of the vascular graft 1 are configured in a similar manner as the configuration of the pressure sensing device 5 and the velocity sensing device 7 shown in FIG. 1 (*b*), respectively.

The pressure sensing device 5 comprises multiple layers. In the unrolled configuration as shown in FIGS. 1(*a*) and 1(*b*), each layer extends in parallel to the main extension plane, i.e., along the first direction 13 and along the second direction 15. A first layer of the multiple layers comprises a first electrode 17, a second layer of the multiple layers comprises a piezoelectric element 19, a third layer of the multiple layers comprises a second electrode 21, and a fourth layer of the layer stack comprises a flexible layer 23. The flexible layer 23 is arranged between the substrate 3 and the first electrode 17 and the piezoelectric element 19 is arranged between the first electrode 17 and the second electrode 21. The thickness of the piezoelectric element 19 perpendicular to the main extension plane, i.e., along a third direction 25 perpendicular to the first direction 13 and perpendicular to the second direction 15, is 2 to 20 μm, preferably 4 μm. The thickness of the flexible layer 23 along the third direction 25 is 2 to 25 μm, preferably 8 μm. The first electrode 17 and the second electrode 21 each comprise gold, Au, and chromium, Cr. The piezoelectric element 19 comprises polyvinylidene difluoride, PVDF, and the flexible layer 23 comprises polyamide, PI.

Similarly, the velocity sensing device 7 comprises multiple layers. In the unrolled configuration as shown in FIGS. 1(*a*) and 1(*b*), each layer extends in parallel to the main extension plane. A first layer of the multiple layers comprises a first electrode 17, a second layer of the multiple layers comprises a piezoelectric element 19, a third layer of the multiple layers comprises a second electrode 21, and a fourth layer of the layer stack comprises a flexible layer 23. The flexible layer 23 is arranged between the substrate 3 and the first electrode 17 and the piezoelectric element 19 is arranged between the first electrode 17 and the second electrode 21. The thickness of the piezoelectric element 19 perpendicular to the main extension plane is 2 to 20 μm, preferably 4 μm. The thickness of the flexible layer 23 along the third direction 25 is 2 to 25 μm, preferably 8 μm. The first electrode 17 and the second electrode 21 each comprise gold, Au, and chromium, Cr. The piezoelectric element 19 comprises polyvinylidene difluoride, PVDF, and the flexible layer 23 comprises polyamide, PI.

The velocity sensing device 7 comprises a cantilever, which comprises the first electrode 17, the piezoelectric element 19, the second electrode 21, and the flexible layer 23 of the velocity sensing device 7. The cantilever extends from a supported end in parallel to the main extension plane towards a free end. The free end is arranged on the first side of the substrate 3 above a portion of a wall, preferably above a portion of a bottom wall, defining a recess 27, which is open towards the first side of the substrate 3. The recess 27 comprises in the unrolled configuration as shown in FIGS. 1(*a*) and 1(*b*) a shape of a rectangular cuboid. The rectangular cuboid comprises an extension along the first direction 13 of 0.5 to 1.5 mm, preferably 1 mm, an extension along the second direction 15 of 0.5 to 1 mm, preferably 0.8 mm, and an extension along the third direction 25 of 0.2 to 1 mm, preferably 0.5 mm.

FIG. 1 (*a*) displays eight paths 9. A first path is coupled with one end to the first electrode 17 of the pressure sensing device 5 shown in the figure on the left. A second path is coupled with one end to the second electrode 21 of the pressure sensing device 5 shown in the figure on the left. A third path is coupled with one end to the first electrode 17 of the pressure sensing device 5 shown in the figure on the right. A fourth path is coupled with one end to the second electrode 21 of the pressure sensing device 5 shown in the figure on the right. A fifth path is coupled with one end to the first electrode 17 of the velocity sensing device 7 shown in the figure on the left. A sixth path is coupled with one end to the second electrode 21 of the velocity sensing device 7 shown in the figure on the left. A seventh path is coupled with one end to the first electrode 17 of the velocity sensing device 7 shown in the figure on the right. An eighth path is coupled with one end to the second electrode 21 of the velocity sensing device 7 shown in the figure on the right. Each of the paths 9 extends in a meandering shape from the respective first end to a respective second end. Each second end is coupled to a respective lead pad 29. Each lead pad 29 extends along the second direction 15 and forms a lead pad 29 of a number of lead pads, which are arranged parallel to each other.

Figure 2:
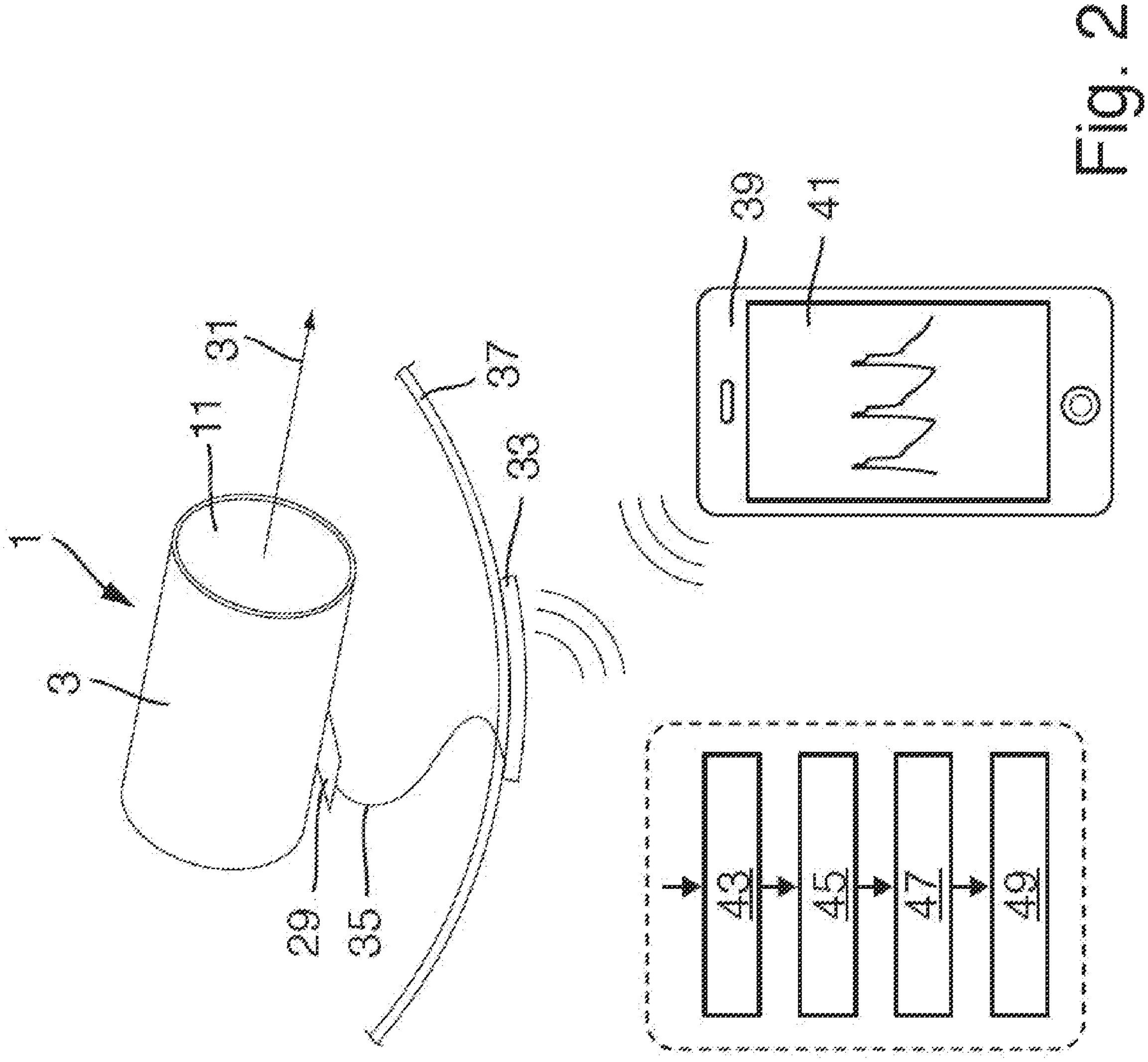
FIG. 2 schematically illustrates the embodiment of the vascular graft of FIGS. 1(*a*) and 1(*b*) in a rolled-up configuration.

FIG. 2 schematically illustrates the embodiment of the vascular graft 1 of FIGS. 1(*a*) and 1(*b*) in a rolled-up configuration. The first surface 11 of the substrate 3 on the first side of the substrate 3 is facing radially inward and a second surface of the substrate 3 on a second side of the substrate 3 is facing radially outward. The substrate 3 comprises the shape of a hollow cylinder, which defines an axial direction 31.

The two pressure sensing devices 5 and the two velocity sensing devices 7 are arranged on the first side of the substrate 3 such that, in the rolled-up configuration shown in FIG. 2, the two pressure sensing devices 5 and the two velocity sensing devices 7 are arranged along a line with a distance between the devices along the line of 1 to 10 mm, particularly preferred 5 mm. The line extends along the axial direction 31 of the substrate 3 in the rolled-up configuration. The free ends of the velocity sensing devices 7 are positioned radially inward of the respective portion of the wall defining the respective recess 27 formed in the flexible substrate 3.

The vascular graft 1 further comprises a flexible encapsulation layer not shown in the figures. The encapsulation layer is arranged on the first side of the substrate 3 such that, in the rolled-up configuration, the flexible encapsulation layer is arranged radially inward of each of the pressure sensing devices 5, each of the velocity sensing devices 7, and each of the electrically conductive paths 9. The encapsulation layer comprises parylene, preferably a chlorinated parylene, particularly preferred parylene C, and the thickness of the encapsulation layer along the third direction 25 is 1 to 10 μm, preferably 5 μm.

In addition to the vascular graft 1, FIG. 2 shows a flexible processing unit 33 connected via leads 35 to the lead pads 29. The flexible processing unit 33 is configured to process signals received from the vascular graft 1 via the leads 35. The flexible processing unit 33 is attached to the skin 37 of a patient and is adapted to send signals via a wireless interface to a user device 39 with a display 41 on which the user can view information derived from signals provided by the two pressure sensing devices 5 and by the two velocity sensing devices 7 and processed by the flexible processing unit 33.

During a surgical procedure, the vascular graft 1 can be provided in the unrolled configuration as shown in FIGS. 1(*a*) and 1(*b*) and can be brought into the rolled-up configuration as shown in FIG. 2. In the rolled-up configuration, the vascular graft 1 can, for example, be connected to two blood vessels such that after the vascular graft 1 is connected to the two blood vessels, the blood flow from one of the two blood vessels is directed through the vascular graft 1 and from the vascular graft 1 to the other one of the two blood vessels. Since in the rolled-up configuration, the first surface 11 of the substrate 3 is facing radially inward, the blood flows along the first surface 11. For example, the blood flows along the axial direction 31. Since the pressure sensing and velocity sensing devices 5, 7 are arranged along the line, which extends along the axial direction 31, the blood passes each of the devices 5, 7 one after the other. The flexible encapsulation layer is arranged radially inward of each of the pressure sensing devices 5, each of the velocity sensing devices 7, and each of the electrically conductive paths 9, and thereby protects each of the pressure sensing devices 5, each of the velocity sensing devices 7, and each of the electrically conductive paths 9 from direct contact with blood.

Depending on the pressure of the blood, particularly the static pressure of the blood, the blood applies a particular mechanical load onto each of the pressure sensing devices 5. The applied mechanical load onto a particular pressure sensing device 5 implies that a mechanical stress is applied to the piezoelectric element 19 of the pressure sensing devices 5 and the mechanical stress applied to the piezoelectric element 19 results in a variation of the electric field extending between the surfaces of the piezoelectric element 19, each surface extends perpendicular to the third direction 25. One of the surfaces of the piezoelectric element 19 is attached to a surface of the first electrode 17 of the pressure sensing device 5 and the other one of the surfaces of the piezoelectric element 19 is attached to a surface of the second electrode 21 of the pressure sensing device 5. Since the first electrode 17 and the second electrode 21 are each coupled to a first end of a respective path 9 and each path 9 is coupled with the second end to the respective lead pad 29, the variation of the electric field due to the applied mechanical load onto each of the pressure sensing devices 5 can be detected from a respective pair of lead pads 29.

The flexible processing unit 33 comprises a charge amplifier 43, a filter 45, a signal processor 47, and a wireless module 49. The flexible processing unit 33 is adapted to process the signals it receives from the lead pads 29 and is adapted to generate signals that comprise information from which the pressure of the blood, particularly the static pressure of the blood, which applies the mechanical load onto a respective pressure sensing device 5, can be inferred. Further, the flexible processing unit 33 is adapted to send the generated signals via the wireless interface to the user device 39. The patient can then view information relating to the pressure of the blood, particularly the static pressure of the blood, displayed on the display 41.

Similarly, depending on the velocity of the blood, the blood applies a particular mechanical load onto each of the velocity sensing devices 7. The cantilever of each velocity sensing device 7 extends from the supported end towards the free end such that the free end is positioned radially inward of a portion of a wall defining the respective recess 27 formed in the substrate 3 and open towards the first side of the substrate 3. Each pair of cantilever and recess 27 is adapted such that blood can enter the recess. Therefore, each cantilever is surrounded by blood from a radially inner side (above the cantilever in FIG. 1 (*b*)) and a radially outer side (below the cantilever in FIG. 1 (*b*), i.e., from the side of the recess 27). Due to the blood flow through the vascular graft 1 and the recess 27, the velocity of the blood at the radially inner side of the cantilever may be higher than the velocity of the blood at the radially outer side of the cantilever. Therefore, the static pressure of the blood at the radially outer side of the cantilever may be higher than the static pressure of the blood at the radially inner side of the cantilever. Therefore, the cantilever may bend towards the radially inner side of the cantilever in case the velocity of the blood at the radially inner side of the cantilever is higher than the velocity of the blood at the radially outer side of the cantilever. The velocity of the blood may vary over time due to the heart muscle pumping blood through the vascular graft 1. For each point in time, depending on the current velocity of the blood, particularly depending on the current difference between the velocity of the blood at the radially inner side of the cantilever and the velocity of the blood at the radially outer side of the cantilever, the blood applies a particular mechanical load onto each of the velocity sensing devices 7, particularly on each of the cantilevers. The applied mechanical load onto a particular velocity sensing device 7 implies that a mechanical stress is applied to the piezoelectric element 19 of the velocity sensing devices 7 and the mechanical stress applied to the piezoelectric element 19 results in a variation of the electric field extending between the surfaces of the piezoelectric element 19, each surface extends perpendicular to the third direction 25. One of the surfaces of the piezoelectric element 19 is attached to a surface of the first electrode 17 of the velocity sensing device 7 and the other one of the surfaces of the piezoelectric element 19 is attached to a surface of the second electrode 21 of the velocity sensing device 7. Since the first electrode 17 and the second electrode 21 are each coupled to a first end of a respective path 9 and each path 9 is coupled with the second end to the respective lead pad 29, the variation of the electric field due to the applied mechanical load onto each of the velocity sensing devices 7 can be detected from a respective pair of lead pads 29.

As already described, the flexible processing unit 33 is adapted to process the signals it receives from the lead pads 29. Further, the flexible processing unit is adapted to generate signals that comprise information from which the velocity of the blood, particularly the difference between the velocity of the blood at the radially inner side of the cantilever and the velocity of the blood at the radially outer side of the cantilever, due to which a particular mechanical load is applied to the respective velocity sensing device 7, can be inferred. Further, the flexible processing unit 33 is adapted to send the generated signals via the wireless interface to the user device 39. The patient can then view information relating to the velocity of the blood, particularly the difference between the velocity of the blood at the radially inner side of the cantilever and the velocity of the blood at the radially outer side of the cantilever, displayed on the display 41.

Therefore, the vascular graft 1 is adapted to provide information from which the pressure and the velocity of the blood can be determined at certain positions in the vascular graft 1. For example, information about the cross section available for the blood to flow through the vascular graft 1 can be derived from the pressure and the velocity of the blood at certain positions in the vascular graft 1. For example, the location, size, and morphology (e.g., shape of a triangle, semi-circle, or rectangle) of a thrombus arranged radially inward of the first surface 11 can be derived.

Figure 3:
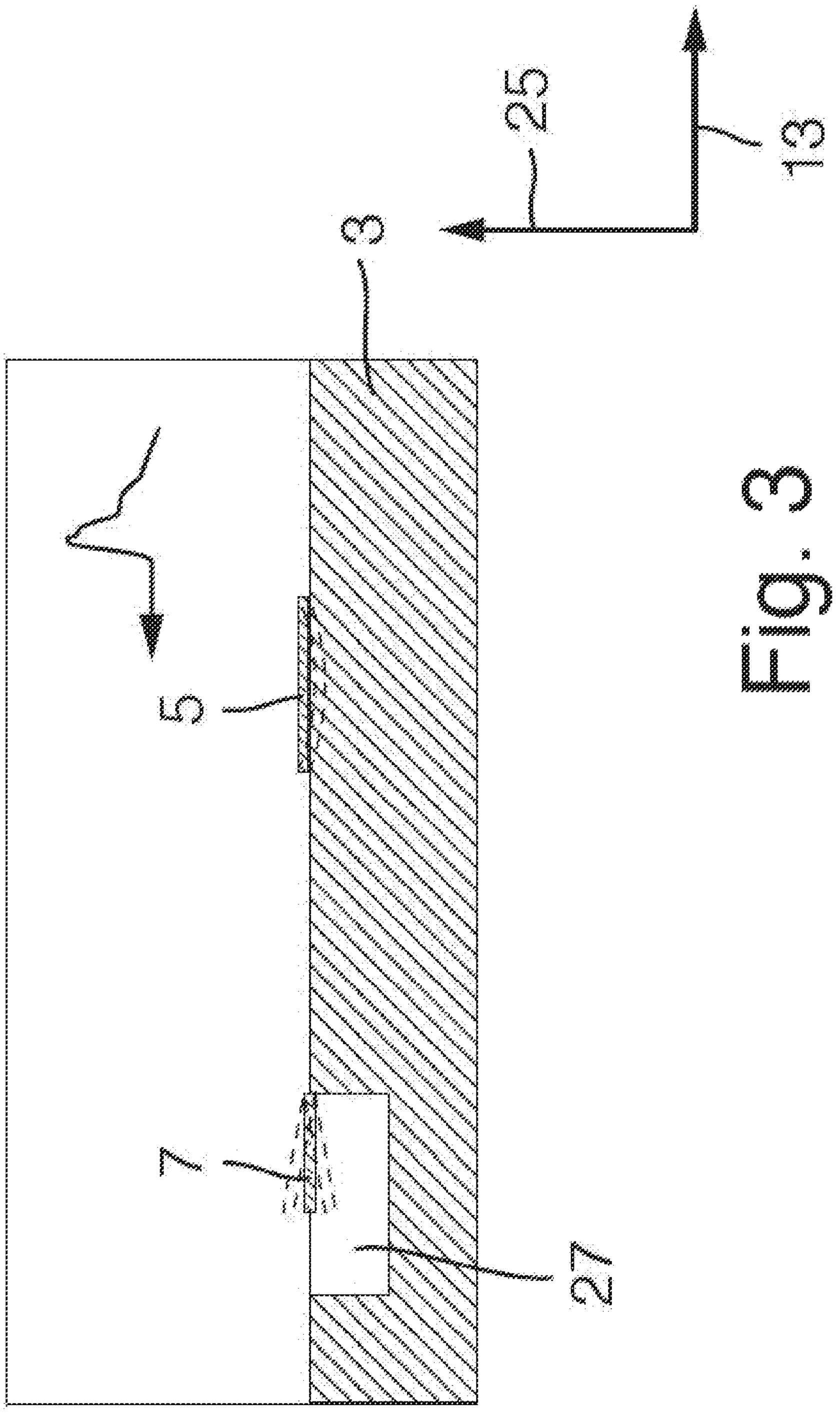
FIG. 3 schematically illustrates a portion of the embodiment of the vascular graft of FIGS. 1(*a*) and 1(*b*) and 2.

FIG. 3 schematically illustrates a portion of the embodiment of the vascular graft 1 of FIGS. 1 and 2. The direction of the blood flow is symbolized by the arrow. As already described, depending on the pressure of the blood, particularly the static pressure of the blood, the blood applies a particular mechanical load onto the pressure sensing device 5. The applied mechanical load onto the pressure sensing device 5 may deform the pressure sensing device 5, which may assume different deformed configurations, each of which corresponds to a particular pressure of the blood. One deformed configuration of the pressure sensing device 5 is symbolized in FIG. 3 by dashed lines. Since the substrate 3 is flexible, each of the pressure sensing devices 5 can be directly attached to the surface of the substrate 3 and each of the pressure sensing devices 5 can deform together with a portion of the substrate 3, which allows a very compact design of the vascular graft 1.

Similarly, as also already described, depending on the velocity of the blood, particularly depending on the difference between the velocity of the blood at the radially inner side of the cantilever and the velocity of the blood at the radially outer side of the cantilever, the blood applies a particular mechanical load onto the velocity sensing device 7. The applied mechanical load onto the velocity sensing device 7 may deform the velocity sensing device 7, which may assume different deformed configurations, each of which corresponds to a particular velocity of the blood, particularly a particular velocity difference. Two deformed configurations of the velocity sensing device 7 are symbolized in FIG. 3 by dashed lines.

Figure 4:
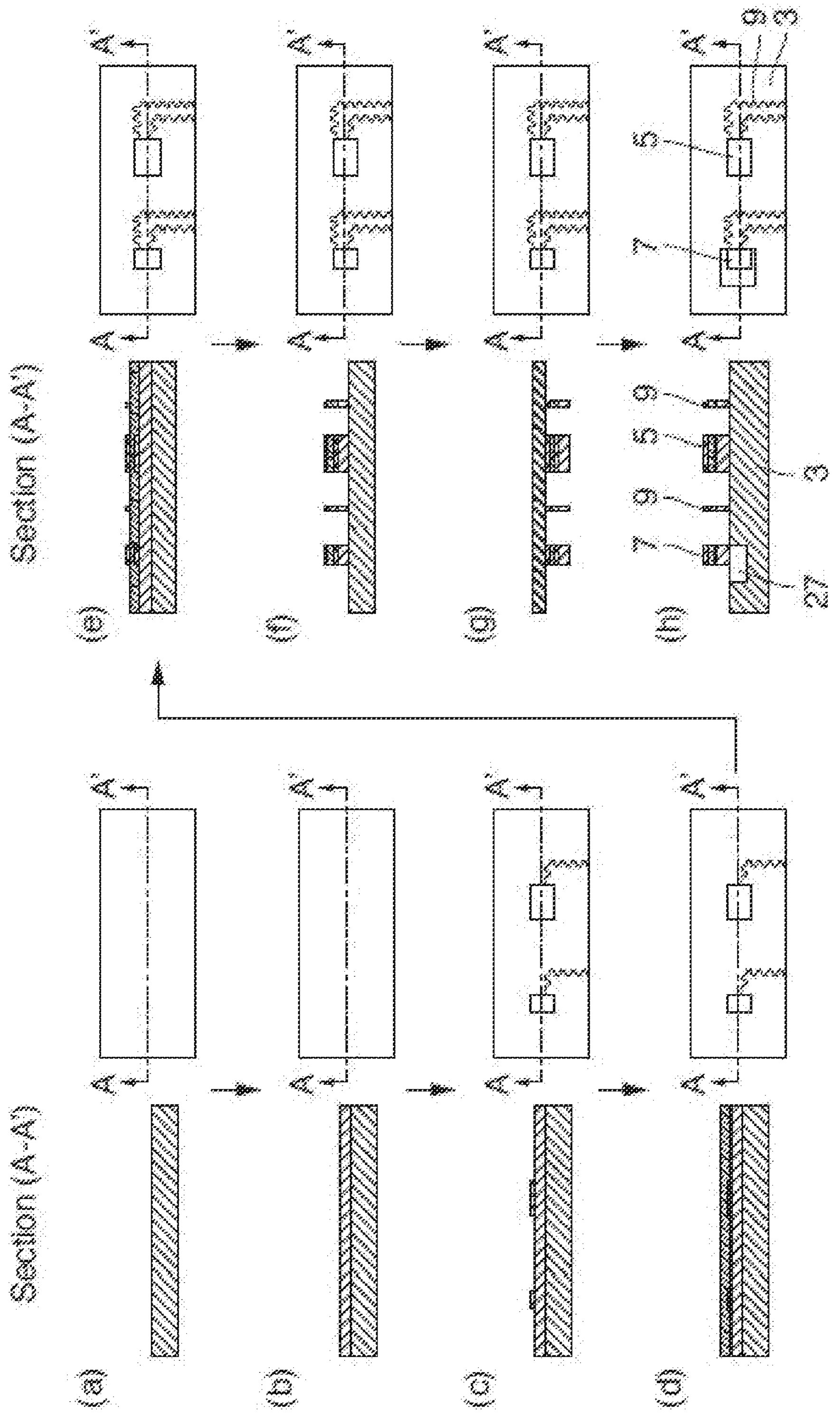
FIG. 4 schematically illustrates a method of manufacturing the vascular graft of FIGS. 1(*a*) to 3.

FIG. 4 schematically illustrates a method of manufacturing the vascular graft 1 of FIGS. 1 to 3. The method comprises eight steps (steps (a) to (h)) and for each step a top view is shown on the right side and a sectional view along the line A-A' in the top view is shown on the left side. Particularly, the vascular graft 1 is manufactured with the assistance of techniques to manufacture microelectromechanical systems (MEMS). In step (a), a single-polished silicon wafer is cleaned with acetone and ethyl alcohol. In step (b), Polyimide (PI) is spin-coated on the silicon wafer and heated in a hot oven at 280° C. for 10 min to form a PI film. In step (c), a sputter-coating Au/Cr (160/40 nm) layer is deposited onto the PI film through a shadow mask. In step (d), a piezoelectric PVDF layer is fabricated. The fabrication of the PVDF layer comprises dissolving PVDF powder in dimethylformamide with a weight fraction 15 wt. %. The fabrication of the PVDF layer further comprises exposing the surface of the PI layer fabricated in step (b) and the surface of the Au/Cr layer on the PI layer fabricated in step (c) to oxygen plasma for 60 s before spin-coating of PVDF to increase the interfacial adhesion both between the PI layer and the PVDF layer and between the Au/Cr layer and the PVDF layer. After spin-coating, the PVDF film is heated using a hot plate at 30° C. for 30 min and then annealed at 100° C. for 2 h with a vacuum drying oven to improve the (3-phase crystallinity.

In step (e), a sputter-coating Au/Cr (160/40 nm) layer is deposited onto the PVDF layer through a shadow mask. In step (f), the layers deposited on top of the silicon wafer are patterned by a reactive ion etching, RIE, process during which a layer of positive photoresist is employed as a mask. In step (g), water-soluble tapes, WSTs, are used as stamps to pick up the patterned layers. In step (h), a flexible Polydimethylsiloxane, PDMS, substrate is fabricated by a PDMS molding process. Negative molds of the required size of the substrate are fabricated by a rapid prototyping process. The PDMS substrate is peeled out of the molds after PDMS casting. The PDMS substrate is then bonded to the patterned layers. PDMS substrate and the WST are exposed to UV-induced ozone, which creates chemical groups between the patterned layers and the PDMS substrate to enhance bonding strength. The patterned layers are attached to the PDMS substrate and the WST, the patterned layers, and the PDMS substrate are heated in an oven at 70° C. for 10 min, which formed strong bonding between the PDMS substrate and the patterned layers. The WST, the patterned layers, and the PDMS substrate are immersed in water to remove WSTs. An encapsulation layer is formed on top of the patterned layers and the PDMS. A uniform encapsulation layer is formed by employing a vacuum evaporator and a 5 μm thick parylene C encapsulation layer is formed to provide a protection against blood and water and an electrical insulation. A dilute isopropyl alcohol-water solution of organic silane gamma-methacrylxypropyltrimethoxysilane is used before parylene C deposition to improve the adhesion significantly. After the deposition of the encapsulation layer, the vascular graft 1 is put on a hot plate at 100° C., and a voltage of 60 V/μm is applied to the lead pads 29 to polarize the piezoelectric PVDF elements 19. After polarization treatment, the lead pads 29 are short-circuited for 24 h.

Figure 5:
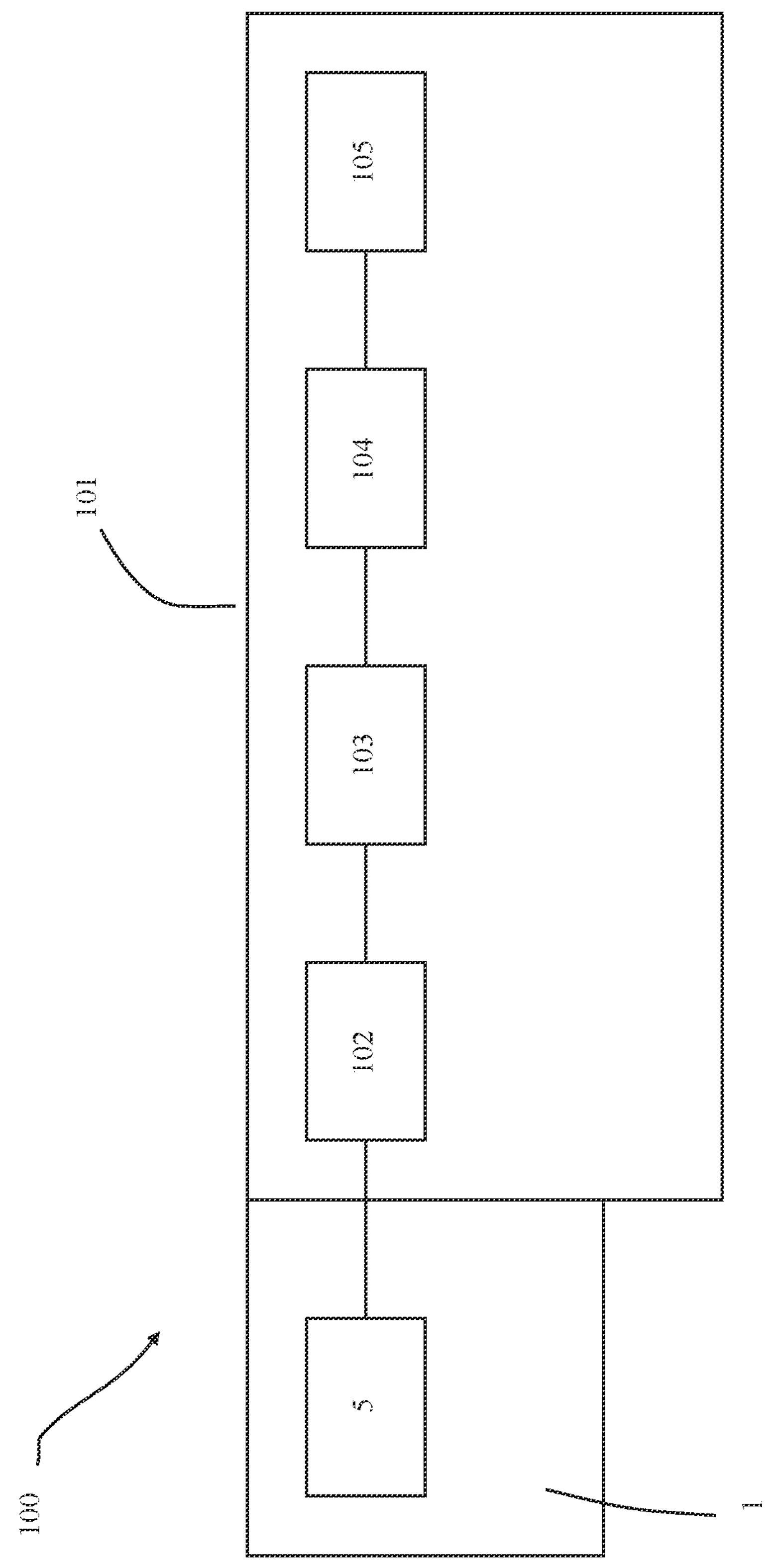
FIG. 5 shows, in schematic form, a vascular graft system according to the invention.

FIGS. 1 to 4 and the accompanying description describe embodiments of the vascular graft 1 of the vascular graft system 100 according to the invention and also a mode of operation in combination with a flexible processing unit 33. Shown in FIG. 5, in schematic form, is a vascular graft system 100 according to the invention. The vascular graft system 100 comprises a vascular graft 1 which in turn comprises a pressure sensing device 5. The vascular graft 1 is similar to the vascular graft 1 of FIGS. 1(*a*) and 1(*b*) but lacks the velocity sensing device 7. In an alternative embodiment of the invention the vascular graft 1 further comprises at least one velocity sensing device 7.

The vascular graft system 100 further comprises a processing unit 101 connected to the pressure sensing device 5 of the vascular graft 1. The processing unit 101 comprises an amplifier 102 which amplifies signals received from the pressure sensing device 5. The processing unit 101 further comprises high and low pass filters 103,104 and a processor 105. The processing unit 101 is configured such that in signals from the amplifier 102 pass through the high pass filter 103 and low pass filter 104 before being received by the processor 105 as shown.

In use the pressure sensing device 5 measures blood pressure in an artery and provides an output voltage signal related to the measured blood pressure. This voltage signal is in the form of an arterial pressure pulse trace 106 which comprises a set of consecutive pressure pulses 107. This arterial pressure pulse trace 106 is received by the amplifier 102 of the processing unit 101. It then passes through the high and low pass filters 103,104 before being received by the processor 105.

Figure 6:
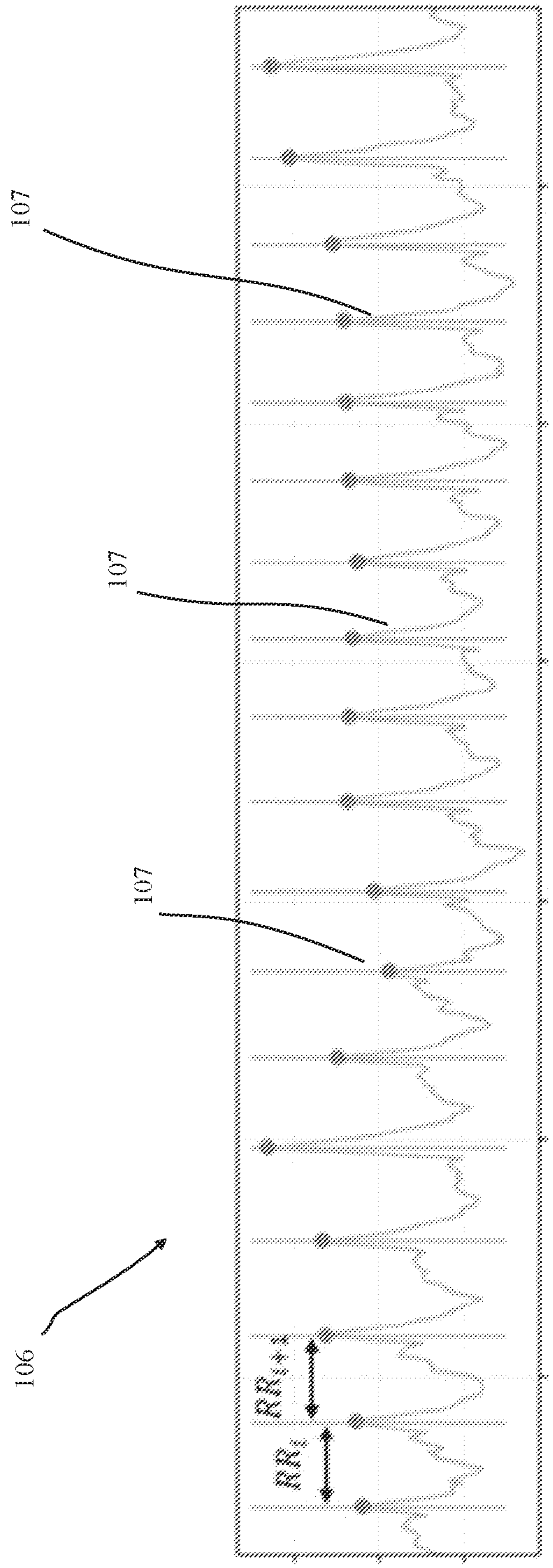
FIG. 6 shows an arterial pressure pulse trace.

The processor 105 de-noises and filters the arterial pressure pulse trace 106. This is typically done by wavelet filtering and convolution. After filtering and de-noising the processor 105 then normalises the pressure pulses 107. A typical arterial pressure pulse trace 106 at this point is shown in FIG. 6.

In a next step for each pressure pulse 107 in the set of pressure pulses 107 the processor 105 classifies the pulse 107 as a regular pulse or an irregular pulse based on its shape. This may be done by the processor 105 comparing each pulse 107 so a set of pre-classified pulses. In the current embodiment however the processor 105 comprises an artificial neural network which classifies each pulse 107 as irregular or regular. The artificial neural network has been trained on a training set of regular and irregular pulses. The processor 105 removes irregular pulses from the set of pressure pulses 107 so producing a reduced set of pressure pulses 107.

Figure 7:
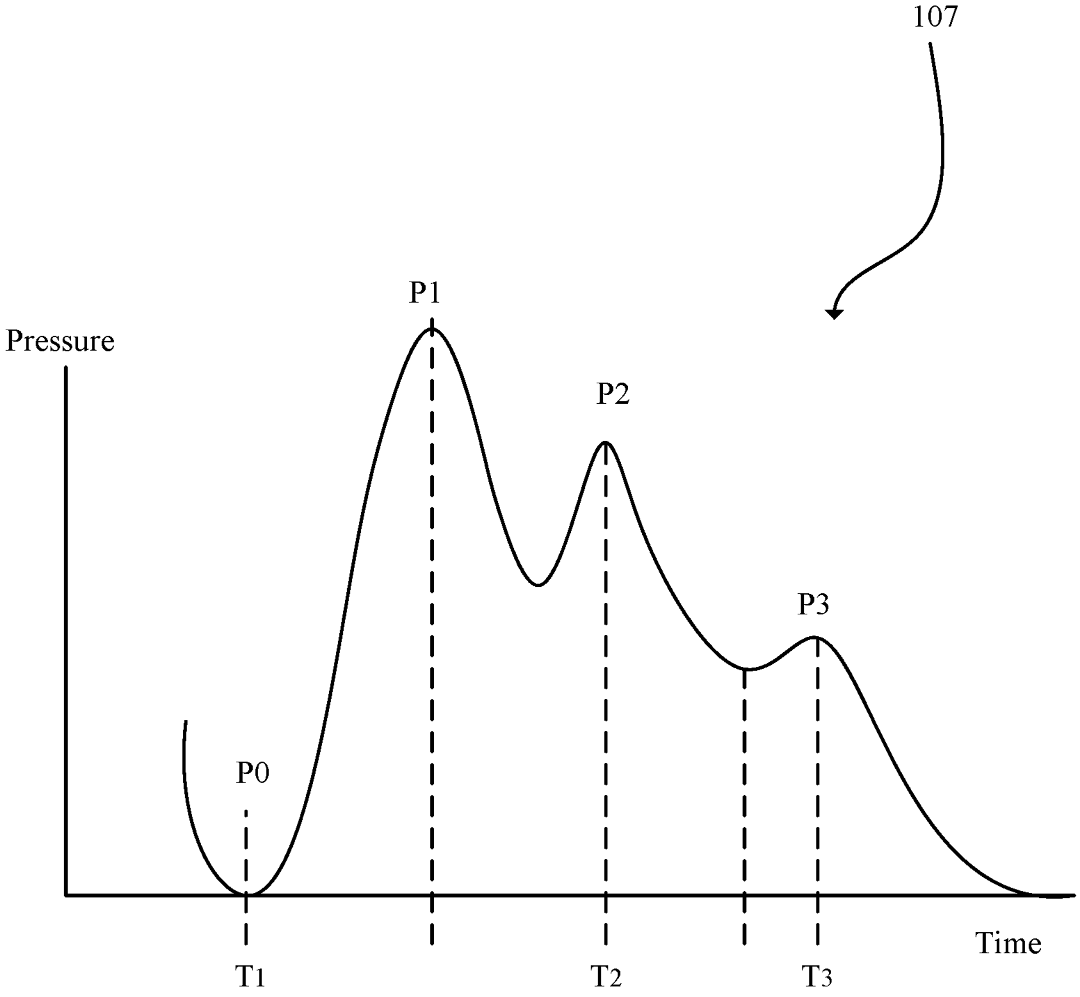
FIG. 7 shows a pressure pulse of an arterial pressure pulse trace.

Shown in FIG. 7 is a typical regular pressure pulse 107 of the reduced set of pressure pulses 107. In FIG. 7, P0, P1, P2, and P3 represents different pressure values at different times (as indicated in the labels on the graph shown in FIG. 7.

In a next step, for each pulse 107 in the reduced set of pressure pulses 107 the processor 105 calculates PWV, SI, AI and K PWV is pulse wave velocity. PWV is calculated by means of the following equation—

$$PWV = 0.8\frac{2\Delta L}{T_2 - T_1}$$

where ΔL is the distance from the aortic arch to the iliac bifurcation which for convenience is set to 0.65. $T_1$ and $T_2$ are the times corresponding to $P_1$ and $P_2$ respectively and the difference between them is the reflected wave transit time.

Stiffness Index (SI) is calculated from the equation $$SI = \frac{H}{PPT}$$

Where H is the height of the subject whose arterial blood pressure is being measured.

AI is the augmentation index. AI is calculated from the equation $$AI = \frac{P_2}{P_1}$$

Finally, K is the mean arterial blood pressure averaged over one pressure pulse 107 and is calculated from the equation $$k = \frac{P_m - P_0}{P_1 - P_0}$$

where $$P_m = \frac{1}{t}\int_0^t P(t)dt$$

and where t is the duration of the pulse

Once PWV, SI, K and AI have been determined the processor 105 compares these to known values and generates an alert if any of these values are abnormal. Classifying the pressure pulses 107 and removing any irregular pulses 107 from the set of pressure pulses 107 before calculating PWV, SI, K and AI improves the accuracy of the calculated results.

In the above embodiment the processor 105 calculates all of PWV, SI, K and AI for each pulse 107. This can be computationally intensive and may also be unnecessary. In an alternative embodiment according to the invention the processor 105 only determines each of PWV, SI, K and AI for a subset of the reduced set of pressure pulses 107. In an alternative embodiment of a vascular graft system 100 according to the invention the processor 105 calculates a subset of PWV, SI, K and AI, preferably only one of PWV, SI, K and AI for some or all of the reduced set of pressure pulses 107.

In a further embodiment of the invention the processor 105 is further configured such that for each pressure pulse 107, i, it determines the time interval $RR_i$ between the $i^{th}$ pressure pulse 107 and the $(i+1)^{th}$ pressure pulse 107. Typically, this is done by determining the position of the peak $P_1$ for each pulse 107 and then determining the difference in time between consecutive peaks.

In a next step, for the two sets of time intervals $$X=\{RR_i/i=1,2,3, \ldots n\}$$

$$Y=\{RR_{i+1}/i=1,2,3, \ldots n\}$$

the processor 105 determines standard deviations SD1 and SD2 from the equations $$SD_1 = \frac{STD(X - Y)}{\sqrt[2]{2}}$$

and $$SD_2 = \frac{STD(X + Y)}{\sqrt[2]{2}}$$

Where STD(X−Y) is the standard deviation of the set of elements $\{X_i - Y_i\}$ and STD (X+Y) is the standard deviation of the set of elements $\{X_i + Y_i\}$.

In a final step the processor 105 compares $SD_1$ to $SD_2$ to produce a pressure result. In this embodiment the pressure result=$SD_1/SD_2$. This result can be used to determine if a user is at a risk of arrhythmia.

Figure 8:
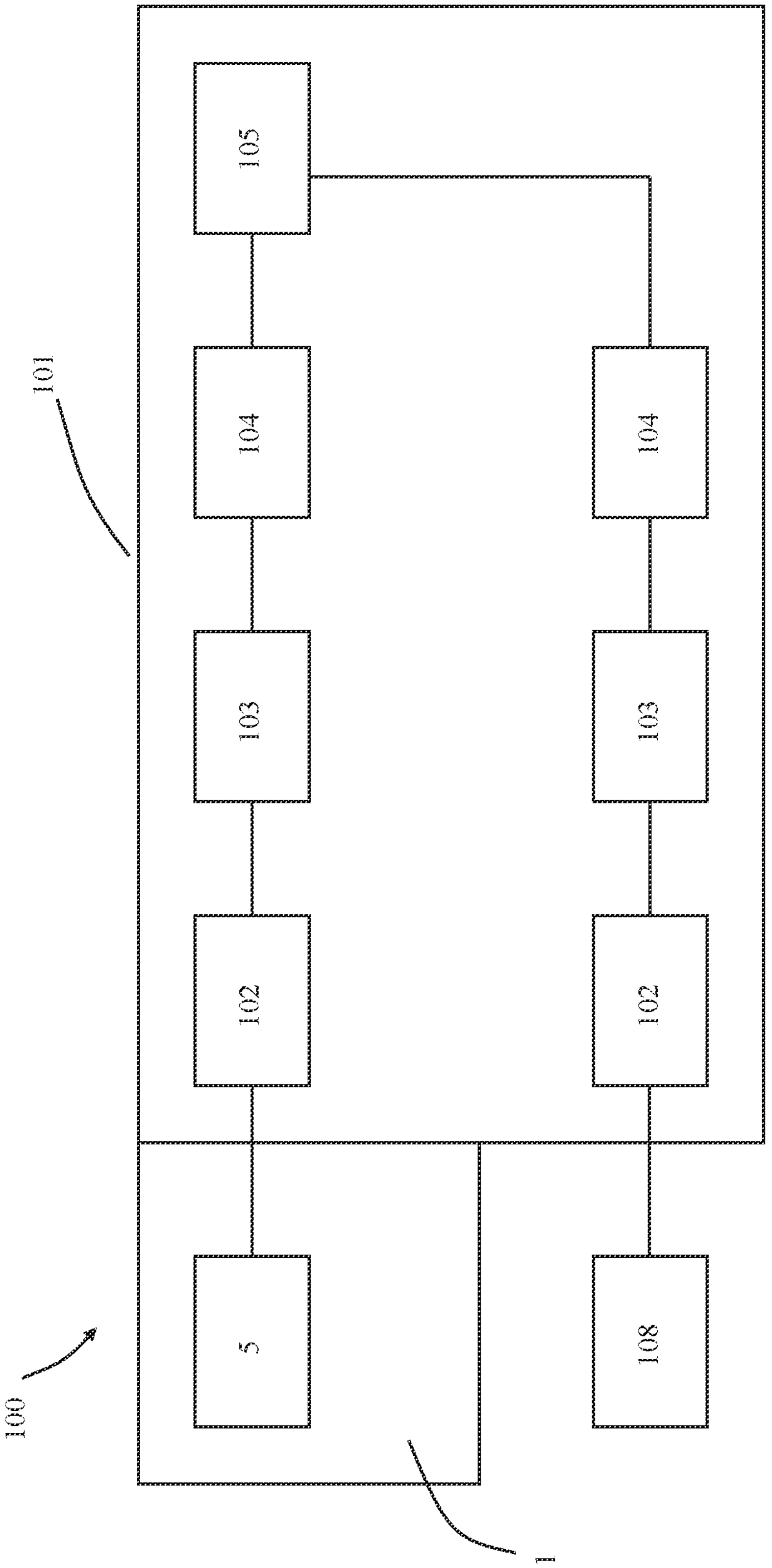
FIG. 8 shows, in schematic form, a further embodiment of a vascular graft system according to the invention.
Figure 9:
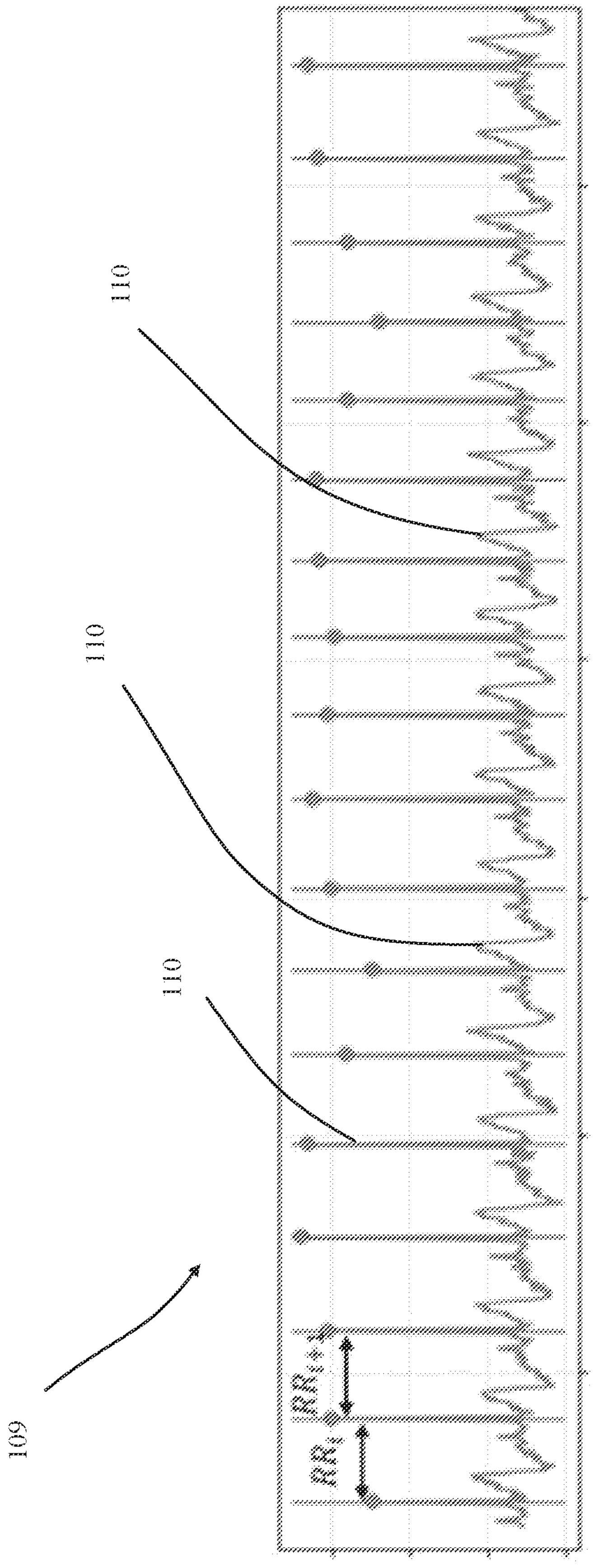
FIG. 9 shows an ECG trace.

Shown in FIG. 8 in schematic form is a further embodiment of a vascular graft system 100 according to the invention. This embodiment is similar to the embodiment of FIG. 5 except it further comprises at least one electrode 108 connected to the processing unit 101. In use the electrode 108 provides an ECG trace 109 which comprises a plurality of consecutive ECG pulses 110 to the processing unit 101. As with the arterial pressure pulse trace 106, the ECG trace 109 passes through an amplifier 102 and then through high and low pass filters 103, 104 before arriving at the processor 105. The processor 105 is configured to de-noise and filter the ECG trace 109. Again, this is typically done by wavelet filtering and convolution. After filtering and de-noising the processor 105 normalises the ECG pulses 110. A typical ECG trace 109 at this point is shown in FIG. 9.

The processor 105 then determines the position in time of the peak of each ECG pulse 110. The processor 105 then performs the steps of (a) for each ECG pulse, i, determine the time interval $RR_i$ between the $i^{th}$ ECG pulse and the $(i+1)^{th}$ ECG pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X - Y)}{\sqrt[2]{2}}$$

$$SD_2 = \frac{STD(X + Y)}{\sqrt[2]{2}}$$

and, (c) compare SD1 to SD2 to obtain an ECG result.

Typically, the ECG result=$SD_1/SD_2$ The ECG result can also be used as a predictor of arrhythmia.

Figure 10:
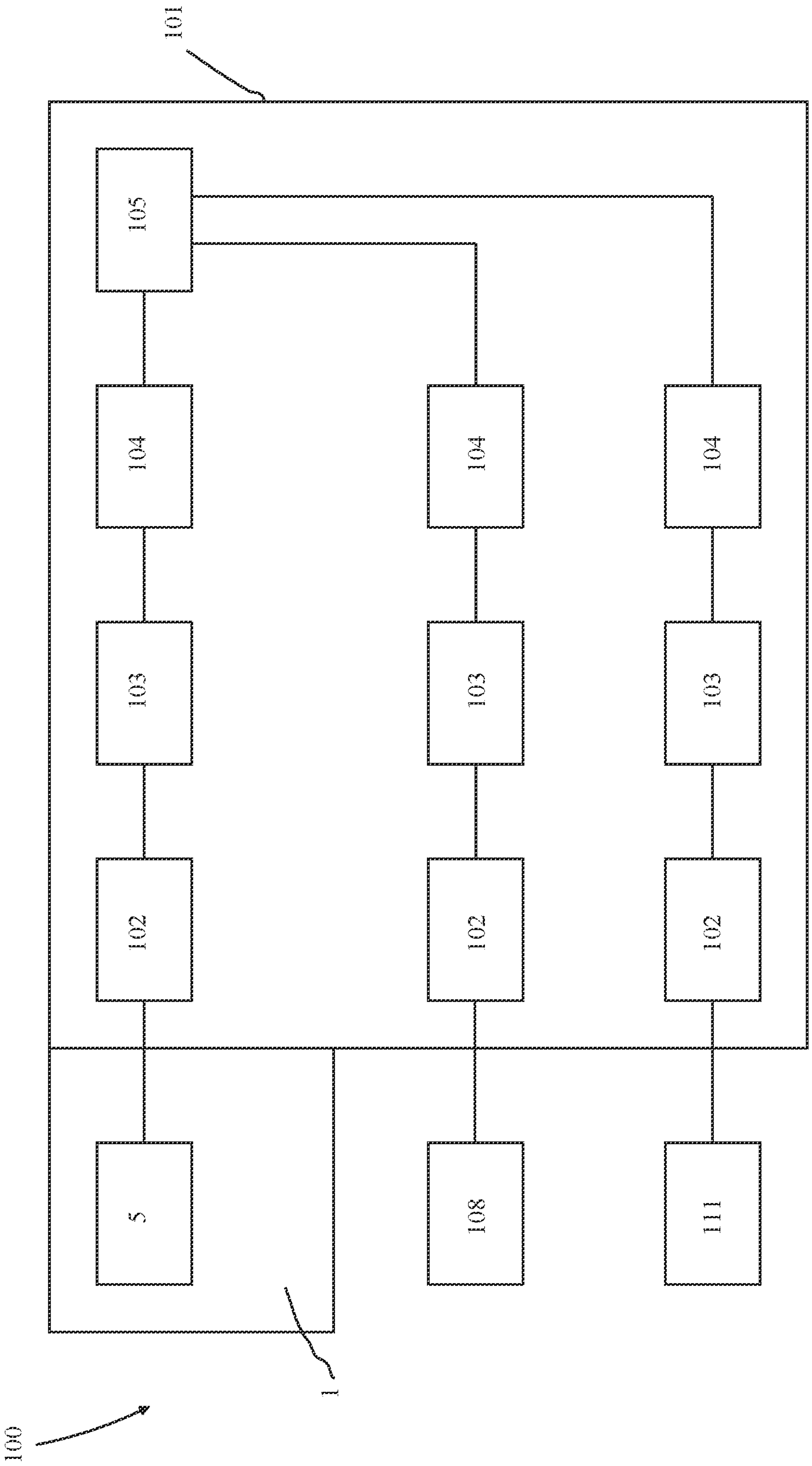
FIG. 10 shows a further embodiment of a vascular graft system according to the invention; and, FIG. 11 shows a PPG trace.
Figure 11:
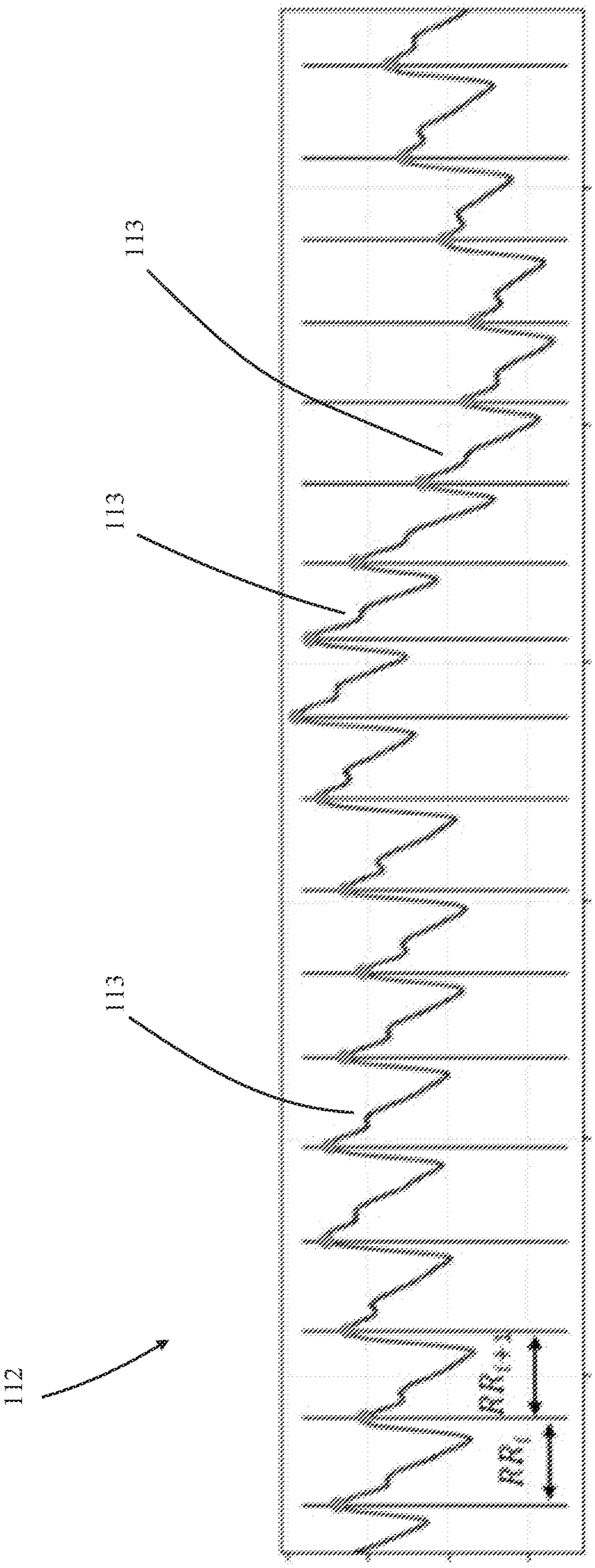

Shown in FIG. 10 in schematic form is a further embodiment of a vascular graft system 100 according to the invention. This embodiment is similar to that of FIG. 8 except it further comprises a pulse oximeter 111 connected to the processing unit 101 In use the pulse oximeter 111 provides a PPG trace 112 which comprises a plurality of consecutive PPG pulses 113 to the processing unit 105. The PPG trace 112 passes through an amplifier 102 and then through high and low pass filters 103,104 before arriving at the processor 105. As before, the processor 105 de-noises and filters the PPG trace 112, typically by wavelet filtering and convolution. The processor 105 then normalises the PPG pulses 113. A typical PPG trace 112 at this point in shown in FIG. 11.

The processor 105 then determines the position in time of the peak of each PPG pulse 113. The processor 105 then performs the steps of (a) for each PPG pulse 113, i, determine the time interval $RR_i$ between the $i^{th}$ PPG pulse 113 and the $(i+1)^{th}$ PPG pulse 113;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X - Y)}{\sqrt[2]{2}}$$

$$SD_2 = \frac{STD(X + Y)}{\sqrt[2]{2}}$$

and, (c) compare SD1 to SD2 to obtain a PPG result.

Typically, the PPG result=$SD_1/SD_2$ The PPG result can be used as a further predictor of arrhythmia.

It is additionally pointed out that "comprising" does not rule out other elements, and "a" or "an" does not rule out a multiplicity. It is also pointed out that features that have been described with reference to one of the above exemplary embodiments may also be disclosed as in combination with other features of other exemplary embodiments described above. Reference signs in the claims are not to be regarded as restrictive.

The invention claimed is:

1. A vascular graft system comprising a vascular graft, the vascular graft comprising a substrate that is flexible, which can assume an unrolled configuration, in which the substrate extends along a main extension plane, and a rolled-up configuration in which a first surface of the substrate on a first side of the substrate is facing radially inward and a second surface of the substrate on a second side of the substrate is facing radially outward; and, at least one pressure sensing device, which is arranged on the first side of the substrate and comprises a first electrode, a second electrode, and a piezoelectric element arranged between the first electrode and the second electrode, and, a processing unit connected to the at least one pressure sensing device, the processing unit comprising a processor configured to perform the steps of (a) receive an arterial pressure pulse trace from the pressure sensor, the arterial pressure pulse trace comprising a set of pressure pulses that are consecutive;

(b) for each pulse in the set of pressure pulses classify the pulse as a regular pulse or an irregular pulse and remove the pulse from the set of pressure pulses if the pulse is an irregular pulse so producing a reduced set of pressure pulses;

(c) for at least one of the pressure pulses in the reduced set of pressure pulses determine at least one of a pulse wave velocity (PWV), a stiffness index (SI), an arterial blood pressure averaged over one pressure pulse (K), or an augmentation index (AI);

and, (d) compare the determined at least one of PWV, SI, K and AI to at least one known value to assess a pulse condition.

2. A vascular graft system as claimed in claim 1, wherein the vascular graft further comprises at least one velocity sensing device which is arranged on the first side of the substrate and comprises a first electrode, a second electrode, and a piezoelectric element arranged between the first electrode and the second electrode.

3. A vascular graft system as claimed in claim 1, wherein the processor is configured to determine at least one of PWV, SI, K and AI for a plurality of pressure pulses.

4. A vascular graft system as claimed in claim 1, wherein the processor is configured such that for at least one pressure pulse it determines each of PWV, SI, K and AI.

5. A vascular graft system as claimed in claim 1, wherein the processor comprises an artificial neural network configured to classify the pressure pulses as irregular or regular.

6. A vascular graft system as claimed in claim 1, wherein the processor is configured to classify the pressure pulses by comparing each pressure pulse with at least one pre-classified pressure pulse.

7. A vascular graft system as claimed in claim 1, wherein the processor is further configured to perform the steps of (a) for each pressure pulse, i, determine the time interval $RR_i$ between the $i^{th}$ pressure pulse and the $(i+1)^{th}$ pressure pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) compare SD1 to SD2 to obtain a pressure result.

8. A vascular graft system as claimed in claim 1 comprising at least one electrode connected to the processing unit for providing an ECG trace to the processor, the ECG trace comprising a set of consecutive ECG pulses, the processor being further configured to perform the steps of (a) for each ECG pulse, i, determine the time interval $RR_i$ between the $i^{th}$ ECG pulse and the $(i+1)^{th}$ ECG pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) compare SD1 to SD2 to obtain an ECG result.

9. A vascular graft system as claimed in claim 1 comprising at least one pulse oximeter connected to the processing unit for providing a PPG trace to the processor, the PPG trace comprising a set of consecutive PPG pulses, the processor being further configured to perform the steps of (a) for each PPG pulse, i, determine the time interval $RR_i$ between the $i^{th}$ PPG pulse and the $(i+1)^{th}$ PPG pulse;

(b) for the two sets of time intervals $$X=\{RR_i/i=1,2,3, \ldots n\}$$

$$Y=\{RR_{i+1}/i=1,2,3, \ldots n\}$$

determine SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) compare SD1 to SD2 to obtain a PPG result.

10. A method of processing an arterial pressure pulse trace comprising the steps of (a) receiving an arterial pressure pulse trace from a vascular graft, the vascular graft comprising at least one pressure sensing device, the arterial pressure pulse trace comprising a set of pressure pulses that are consecutive;

(b) for each pressure pulse in the set of pressure pulses classifying the pulse as a regular pulse or an irregular pulse and removing the pulse from the set of pressure pulses if the pulse is an irregular pulse so producing a reduced set of pressure pulses;

(c) for at least one of the pressure pulses in the reduced set of pressure pulses, determining at least one of a pulse wave velocity (PWV), a stiffness index (SI), an arterial blood pressure averaged over one pressure pulse (K), or an augmentation index (AI); and, (d) comparing the determined at least one of PWV, SI, K and AI to at least one known value to assess a pulse condition, wherein the vascular graft comprises a substrate that is flexible with an unrolled configuration, in which the substrate extends along a main extension plane, and a rolled-up configuration in which a first surface of the substrate on a first side of the substrate is facing radially inward and a second surface of the substrate on a second side of the substrate is facing radially outward;

wherein the at least one pressure sensing device is arranged on the first side of the substrate and comprising a first electrode, a second electrode, and a piezoelectric element arranged between the first electrode and the second electrode.

11. A method as claimed in claim 10, wherein the vascular graft further comprises at least one velocity sensing device which is arranged on the first side of the substrate and comprises a first electrode, a second electrode, and a piezoelectric element arranged between the first electrode and the second electrode.

12. A method as claimed in claim 10, wherein the step of for at least one of the pressure pulses in the reduced set of pressure pulses determining at least one of PWV, SI, K and AI comprises determining at least one of PWV, SI, K and AI for a plurality of pressure pulses.

13. A method as claimed in claim 10, wherein the step of for at least one of the pressure pulses in the reduced set of pressure pulses determining at least one of PWV, SI, K and AI comprises determining each of PWV, SI, K and AI for at least one pressure pulse.

14. A method as claimed in claim 10, wherein the step of for each pressure pulse in the set of pressure pulses classifying the pulse as a regular pulse or an irregular pulse comprises providing each pulse to an artificial neural network for classification.

15. A method as claimed in claim 10, wherein the step of for each pressure pulse in the set of pressure pulses classifying the pulse as a regular pulse or an irregular pulse comprises comparing each pulse with at least one pre-classified pressure pulse.

16. A method as claimed in claim 10, further comprising the steps of (a) for each pressure pulse, i, determining the time interval $RR_i$ between the $i^{th}$ pressure pulse and the $(i+1)^{th}$ pressure pulse;

(b) for the two sets of time intervals $$X=\{RR_i/i=1,2,3, \ldots n\}$$

$$Y=\{RR_{i+1}/i=1,2,3, \ldots n\}$$

determining SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (c) comparing SD1 to SD2 to obtain a pressure result.

17. A method as claimed in claim 10, further comprising the steps of (a) receiving a ECG trace, the ECG trace comprising a set of consecutive ECG pulses;

(b) for each ECG pulse, i, determining the time interval $RR_i$ between the $i^{th}$ ECG pulse and the $(i+1)^{th}$ ECG pulse;

(c) for the two sets of time intervals $$X=\{RR_i/i=1,2,3, \ldots n\}$$

$$Y=\{RR_{i+1}/i=1,2,3, \ldots n\}$$

determining SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (d) comparing SD1 to SD2 to obtain an ECG result.

18. A method as claimed in claim 10, further comprising the steps of (a) receiving a PPG trace, the PPG trace comprising a set of consecutive PPG pulses;

(b) for each PPG pulse, i, determining the time interval $RR_i$ between the $i^{th}$ PPG pulse and the $(i+1)^{th}$ PPG pulse;

(c) for the two sets of time intervals $$X=\{RR_i/i=1,2,3, \ldots n\}$$

$$Y=\{RR_{i+1}/i=1,2,3, \ldots n\}$$

determining SD1 and SD2 from the equations $$SD_1 = \frac{STD(X-Y)}{\sqrt[2]{2}}$$

$$SD_2 = \frac{STD(X+Y)}{\sqrt[2]{2}}$$

and, (d) comparing SD1 to SD2 to obtain a PPG result.

* * * * *